(12) United States Patent
Kim et al.

(10) Patent No.: US 8,476,474 B2
(45) Date of Patent: Jul. 2, 2013

(54) ASYMMETRIC STYRYL DERIVATIVES AND ORGANIC LIGHT EMITTING DIODE PREPARED USING THE SAME

(75) Inventors: Tae-Hyung Kim, Yongin-si (KR); Jin-Seok Hong, Suwon-si (KR); Kyoung-Soo Kim, Daejeon (KR); Sang-Do Lee, Yongin-si (KR)

(73) Assignee: Doosan Corporation, Seoul (KR)

( * ) Notice: Subject to any disclaimer, the term of this patent is extended or adjusted under 35 U.S.C. 154(b) by 788 days.

(21) Appl. No.: 12/524,530

(22) PCT Filed: Jan. 25, 2008

(86) PCT No.: PCT/KR2008/000475
§ 371 (c)(1),
(2), (4) Date: Jul. 24, 2009

(87) PCT Pub. No.: WO2008/091130
PCT Pub. Date: Jul. 31, 2008

(65) Prior Publication Data
US 2010/0081846 A1     Apr. 1, 2010

(30) Foreign Application Priority Data
Jan. 26, 2007  (KR) .................. 10-2007-0008160

(51) Int. Cl.
*C07C 211/00*     (2006.01)
(52) U.S. Cl.
USPC .......................................... 564/305; 564/307
(58) Field of Classification Search
None
See application file for complete search history.

(56) References Cited

U.S. PATENT DOCUMENTS 6,242,648 B1     6/2001  Yamasaki et al.
2005/0227465 A1  10/2005  Smith et al.

FOREIGN PATENT DOCUMENTS

| JP | 2000-256276 A | 9/2000 |
| JP | 2001-106658 A | 4/2001 |
| JP | 2002-341570 A | 11/2002 |
| JP | 2004196716 * | 7/2004 |
| JP | 2005-516059 A | 6/2005 |
| JP | 2007-160563 A | 6/2007 |
| JP | 2007-254386 A | 10/2007 |
| WO | 03/064373 A1 | 8/2003 |
| WO | 2005/099312 A2 | 10/2005 |
| WO | WO 2006112582 * | 10/2006 |
| WO | 2008/156089 A1 | 12/2008 |

OTHER PUBLICATIONS

Jou et al., "Hole-Transporting-Layer-Free High-Efficiency Fluorescent Blue Organic Light-Emitting Diodes," 2007, Applied Physics Letters, vol. 91, pp. 1-3.
Japanese Patent Office, JP Office Action issued in corresponding JP Application No. 2009-547176, dated Mar. 4, 2013.

* cited by examiner

*Primary Examiner* — Sudhakar Katakam
*Assistant Examiner* — Clinton Brooks
(74) *Attorney, Agent, or Firm* — Sughrue Mion, PLLC

(57) ABSTRACT

Disclosed are asymmetric styryl derivatives and an organic light emitting diode prepared using the same. More particularly, there are provided asymmetric styryl derivatives that can provide a blue organic light emitting diode with superior thermal stability, as well as improved luminous efficiency, improved brightness, and extended lifetime, by synthesizing a novel thermally stable compound with a styryl structure represented by Formula 1, and using the compound as a dopant in an organic light emitting layer (EML) of a multi-layered organic light emitting diode, and an organic light emitting diode prepared by the same.

6 Claims, 4 Drawing Sheets

ASYMMETRIC STYRYL DERIVATIVES AND ORGANIC LIGHT EMITTING DIODE PREPARED USING THE SAME

TECHNICAL FIELD

The present invention relates to asymmetric styryl derivatives and an organic light emitting diode prepared using the same, and more particularly to asymmetric styryl derivatives that can provide a blue organic light emitting diode with superior thermal stability, as well as improved luminous efficiency, improved brightness, and extended lifetime, by synthesizing a novel thermally stable compound with a styryl structure represented by Formula 1 of the present invention, and using the compound as a dopant in an organic light emitting layer (EML) of a multilayered organic light emitting diode, and an organic light emitting diode prepared by the same.

BACKGROUND ART

An organic light emitting diode (OLED), which is also referred to as organic EL (electroluminescence), is a light emitting device utilizing the principle that a fluorescent material emits light by recombination energy of a hole injected from an anode and an electron injected from a cathode when an electric field is formed by the organic (low molecular weight or polymer) semiconductor of a conjugated structure as a light-emitting material inserted between both electrodes. Such an OLED is the latest high-tech display device that has been widely used for outer and inner windows of a cellular phone, displays of an MP3 and a digital camera, and so forth in recent years, and is expected to be also applicable to a wall-mounted type TV and a flexible TV succeeding PDP and LCD TVs due to low power consumption, a high response speed, and a wide viewing angle.

Various kinds of light emitting device materials comprising organic materials have been developed since a low-voltage-driven OLED using a laminated structure was reported by C. W. Tang et al. of Eastman Kodak Co. in 1987 (C. W. Tang, S. A. Vanslyke, Applied Physics Letters, Vol. 51, p. 913, 1987), and an OLED with a double structure including two organic layers disposed between an anode and a cathode was proposed in U.S. Pat. No. 4,356,429.

An OLED includes a cathode, electron injecting/transporting layers (EIL/ETL), a light emitting layer (EML), hole injecting/transporting layers (HIL/HTL), an anode, a substrate, and the like, and particularly the EML comprises an organic material. One of typical compounds used as the EML material is Alq3, and much research has been done on quinoline complex derivatives, in the course of which some blue light emitting layer materials, such as DPVBi, etc., were also discovered.

A dopant is a material that has a great effect on improving luminous efficiency, but there has been a difficulty in developing the dopant because of insufficient luminous efficiency, discordance with a host material, and so forth. In particular, a blue dopant is difficult to increase purity because a styryl structure is not thermally stable, and thus there is a problem in that color purity or efficiency is lowered or lifetime is shortened. Also, in order to provide deep blue color purity, a band gap between the HOMO and the LUMO of a dopant must be large, but it is not easy to develop such a dopant material.

DISCLOSURE

Technical Problem

Therefore, the present invention has been made in view of the above-mentioned problems. The present inventors have discovered that when an asymmetric styryl derivative represented by Formula 1 of the present invention is synthesized and is used as a light emitting material of an OLED with a multilayered structure, it is possible to provide a blue OLED with superior thermal stability, as well as improved luminous efficiency, improved brightness, and extended life time. Base upon this, the present inventors have finally completed the present invention.

The present invention provides an asymmetric styryl derivative represented by Formula 1, which is thermally stable.

Further, the present invention provides an organic light emitting layer prepared using an asymmetric styryl derivative of the present invention.

Further, present invention provides an OLED comprising an organic light emitting layer prepared using an asymmetric styryl derivative of the present invention.

Technical Solution

In accordance with an aspect of the present invention, there is provided an asymmetric styryl derivative represented by the following Formula 1:

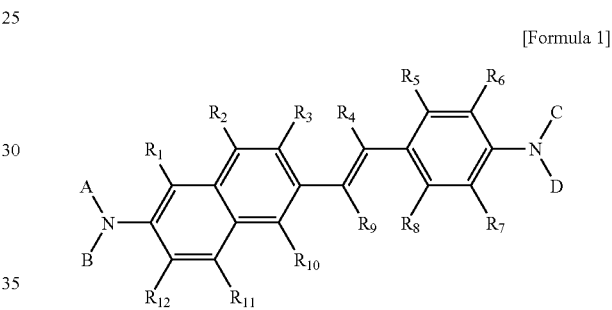

[Formula 1]

In Formula 1, $R_1$ to $R_{12}$ may be the same or different, and each independently represents hydrogen, deuterium, a substituted or unsubstituted $C_1$~$C_{30}$ alkyl group, a substituted or unsubstituted $C_1$~$C_{30}$ alkoxy group, a substituted or unsubstituted $C_6$~$C_{40}$ aryl group, a substituted or unsubstituted $C_6$~$C_{40}$ aryloxy group, a substituted or unsubstituted $C_1$~$C_{30}$ heterocyclic group, an amino group, an alkylamino group, a cyano group, a nitro group, a hydroxyl group, or a halogen atom;

A, B, C, and D may be the same or different, and each independently represents a substituted or unsubstituted phenyl group, a substituted or unsubstituted phenylene group, a substituted or unsubstituted naphthalene group, a substituted or unsubstituted $C_1$~$C_{40}$ aryl group, a substituted or unsubstituted biphenyl group, a substituted or unsubstituted anthracene group, or a substituted or unsubstituted $C_1$~$C_{30}$ alkyl group; and the substituted groups are each independently substituted with one or more kinds of substituents selected from the group consisting of a halogen atom, a $C_1$~$C_{30}$ alkyl group, a $C_1$~$C_{30}$ alkoxy group, a $C_6$~$C_{40}$ aryloxy group, a $C_6$~$C_{40}$ arylalkyl group, a nitro group, a cyano group, an amino group in which a hydrocarbon of $C_1$~$C_{30}$ is substituted, a $C_6$~$C_{40}$ aryl group, and a $C_1$~$C_{30}$ heterocyclic group.

Hereinafter, the present invention will be described in more detail.

The present invention provides an asymmetric styryl derivative that can provide a blue OLED with superior thermal stability, as well as improved luminous efficiency, improved brightness, and extended lifetime, by synthesizing a novel thermally stable compound with a styryl structure represented by Formula 1 of the present invention, and using the compound as a dopant in an organic light emitting layer (EML) of a multilayered OLED, and an OLED prepared by the same.

The substituent groups in Formula 1 are defined as follows:

Typical examples of the substituted or unsubstituted $C_1$~$C_{30}$ alkyl group include, but are limited to, a methyl group, an ethyl group, a propyl group, an isopropyl group, a butyl group, a sec-butyl group, a tert-butyl group, a pentyl group, a hexyl group, a heptyl group, an octyl group, a stearyl group, 2-phenylisopropyl group, a trichloromethyl group, a trifluoromethyl group, a benzyl group, an a-phenoxybenzyl group, an a,a-dimethylbenzyl group, an a,a-methylphenyl-benzyl group, an a,a-ditrifluoromethylbenzyl group, a triphenylmethyl group, etc.

Typical examples of the substituted or unsubstituted $C_1$~$C_{30}$ alkoxy group include, but are limited to, alkoxy groups derived from the above substituted or unsubstituted alkyl group, such as a methoxy group, an ethoxy group, a butoxy group, etc.

Typical examples of the substituted or unsubstituted $C_6$~$C_{40}$ aryl group include, but are not limited to, a phenyl group, a 2-methylphenyl group, a 3-methylphenyl group, a 4-methylphenyl group, a 4-ethylphenyl group, a biphenyl group, a 4-methylbiphenyl group, a 4-ethylbiphenyl group, a 4-cyclohexylbiphenyl group, a terphenyl group, a 3,5-dichlorophenyl group, a naphthyl group, a 5-methylnaphthyl group, an anthryl group, a pyrenyl group, etc.

Typical examples of the substituted or unsubstituted $C_6$~$C_{40}$ aryloxy group include, but are not limited to, a phenoxyl group, a naphthyloxyl group, an anthryloxyl group, a pyrenyloxyl group, a fluorantenyloxyl group, a chrysenyloxyl group, a perylenyloxyl group, etc.

Typical examples of the substituted or unsubstituted $C_1$~$C_{30}$ heterocyclic group include, but are not limited to, a thiophene group, a furan group, a pyrrole group, an imidazole group, a thiazole group, an oxazole group, an oxadiazole group, a triazole group, a pyridyl group, a pyrazine group, a quinolinyl group, an isoquinoline group, an acridly group, a benzothiazole group, a thiodiazole group, etc.

In the asymmetric styryl derivative represented by Formula 1, the substituent groups may be substituted or unsubstituted. When substituted, they may be substituted with one or more kinds of substituents including, but not limited to, a halogen atom, such as a fluorine atom, a chlorine atom, a bromine atom, and an iodine atom; a $C_1$~$C_{30}$ alkyl group, such as a methyl group, an ethyl group, an n-propyl group, and an isopropyl group; a $C_1$~$C_{30}$ alkoxy group, such as a methoxy group and an ethoxy group; a $C_6$~$C_{40}$ aryloxy group, such as a phenoxy group; a $C_6$~$C_{40}$ arylalkyl group, such as a benzyl group, a phenethyl group, and a phenylpropyl group; a nitro group; a cyano group; an amino group in which a hydrocarbon of $C_1$~$C_{30}$ is substituted, such as a dimethylamino group, a dibenzylamino group, a diphenylamino group, and a porpholino group; a $C_6$~$C_{40}$ aryl group, such as a phenyl group, a tolyl group, a biphenyl group, a naphthyl group, an anthryl group, and a pyrenyl group; a $C_1$~$C_{30}$ heterocyclic group, such as a pyridyl group, a tiethyl group, a furyl group, a quinolyl group, and a carbazolyl group; and the like.

The inventive compound represented by Formula 1 can be used as a dopant in an organic light emitting layer, and typical examples of a host that may be used therewith include, but are limited to, ADN (9,10-di(naphthalene-2-yl)anthracene), the AN7 compound disclosed in US Patent Laid-Open No. 2006/0043858, etc.

The doping amount of the compound represented by Formula 1 is not limited to a specific range, but the compound may be preferably doped in an amount of 1 to 20% with respect to an organic light emitting layer so as to ensure the effects of the present invention.

Typical examples of the inventive asymmetric styryl derivative represented by Formula 1 include the following compounds:

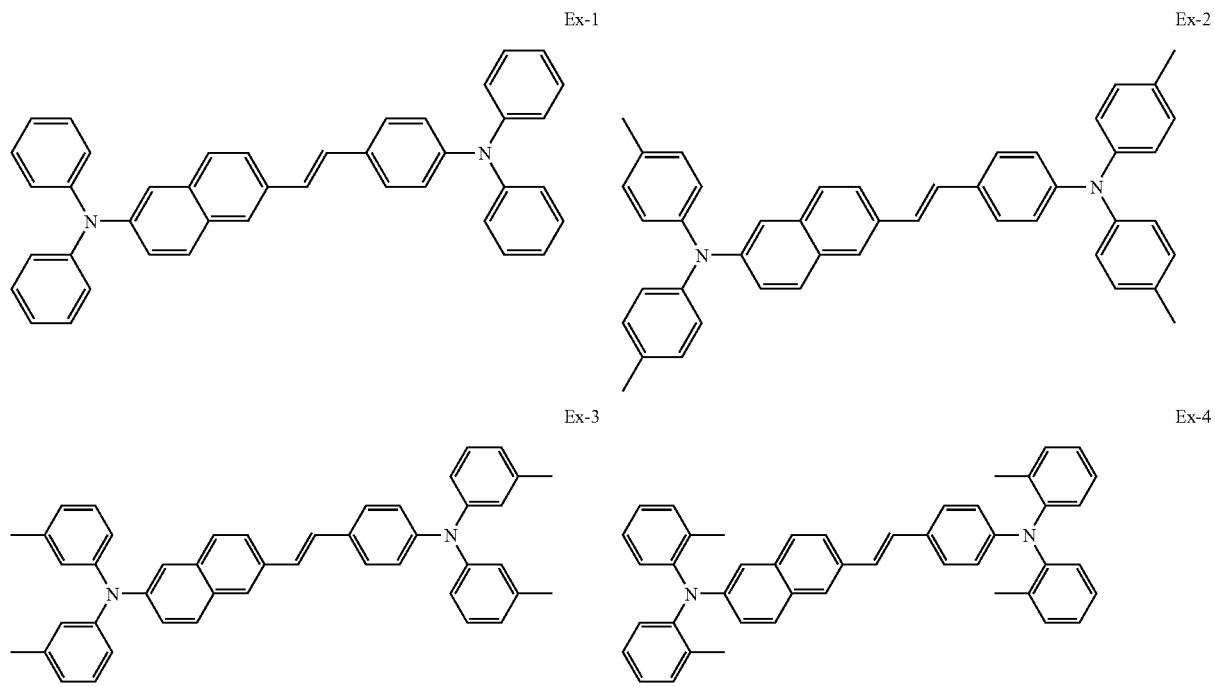

Ex-1

Ex-2

Ex-3

Ex-4

-continued
Ex-5
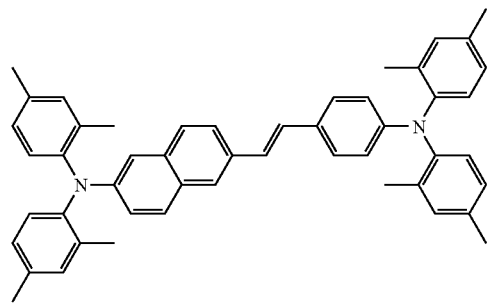
Ex-6
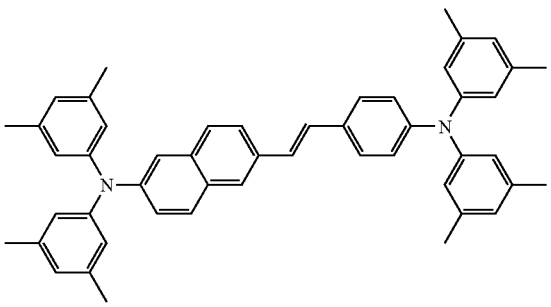
Ex-7
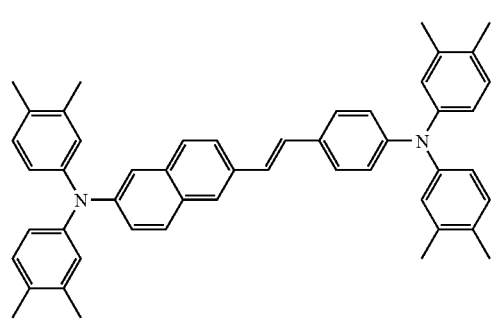
Ex-8
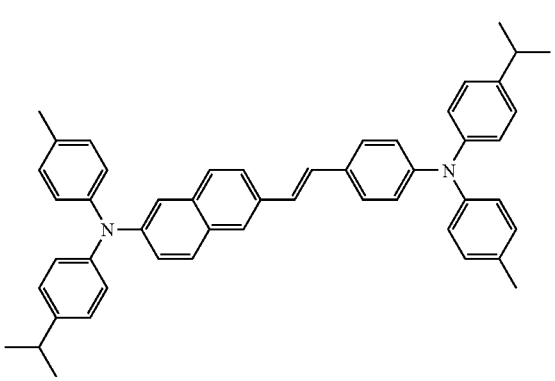
Ex-9
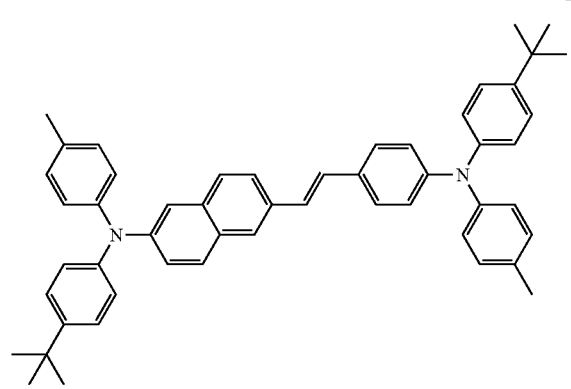
Ex-10
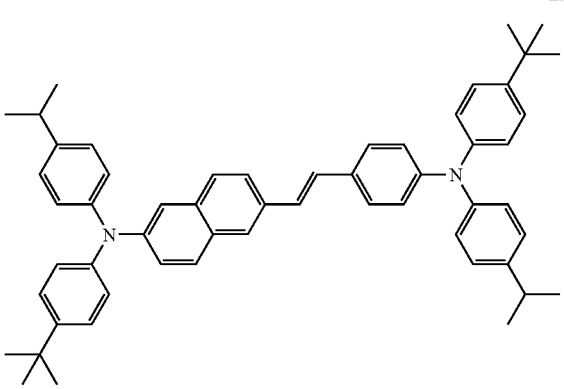
Ex-11
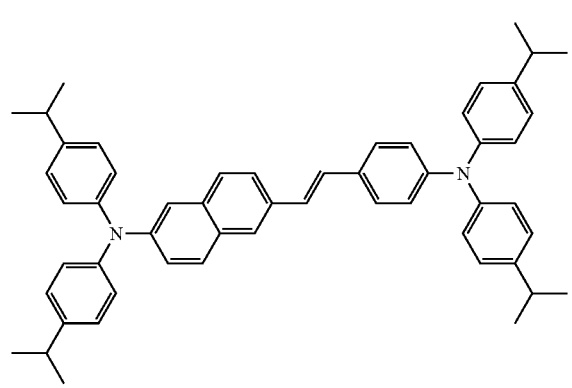
Ex-12
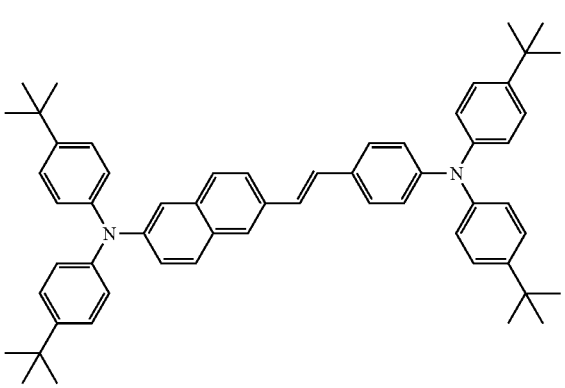

-continued
Ex-13
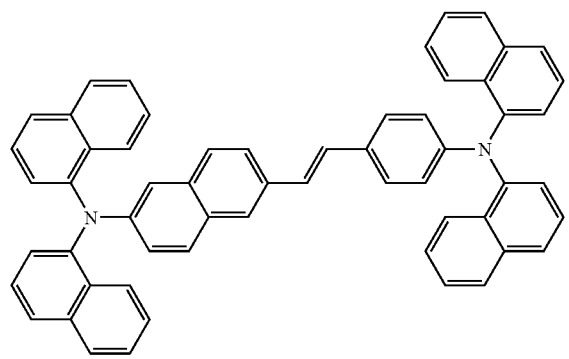
Ex-14
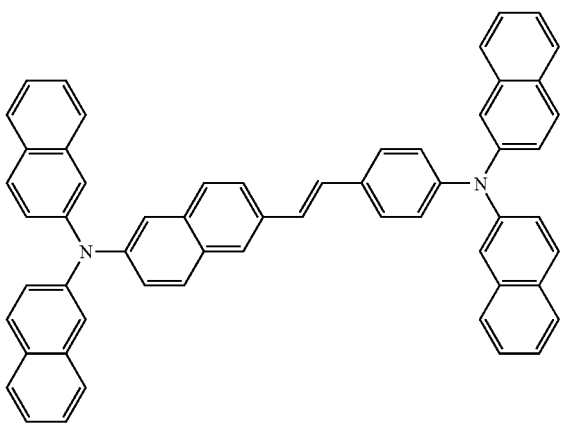
Ex-15
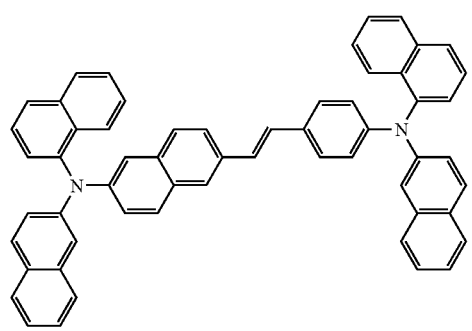
Ex-16
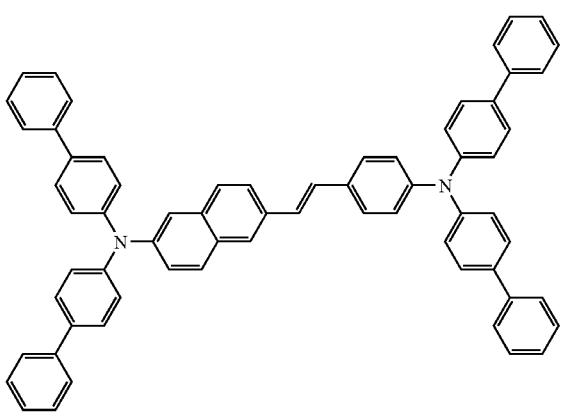
Ex-17
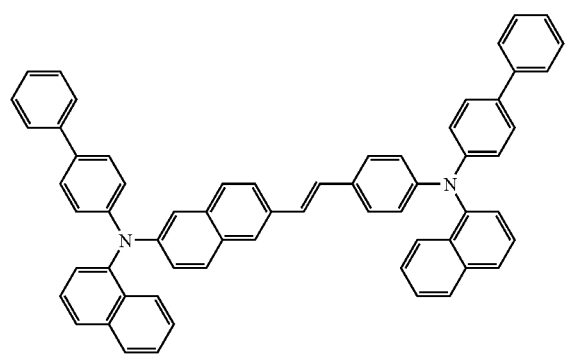
Ex-18
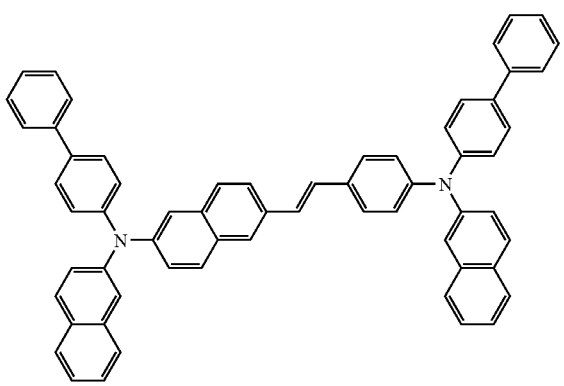
Ex-19
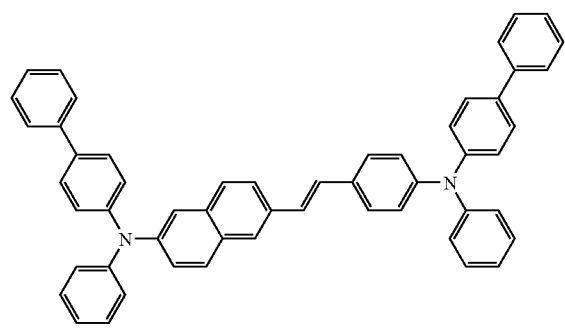
Ex-20
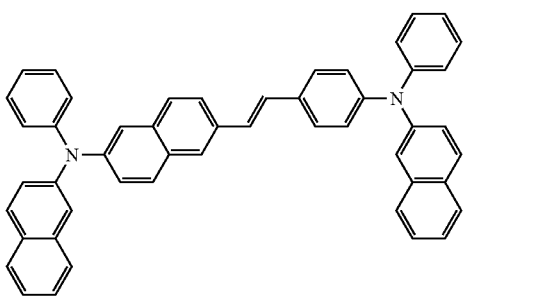

-continued
Ex-21
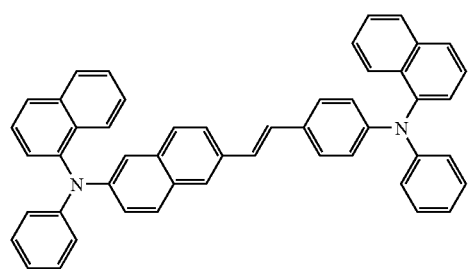
Ex-22
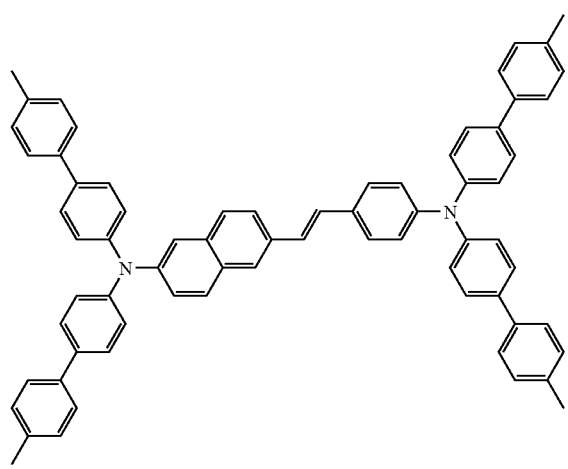
Ex-23
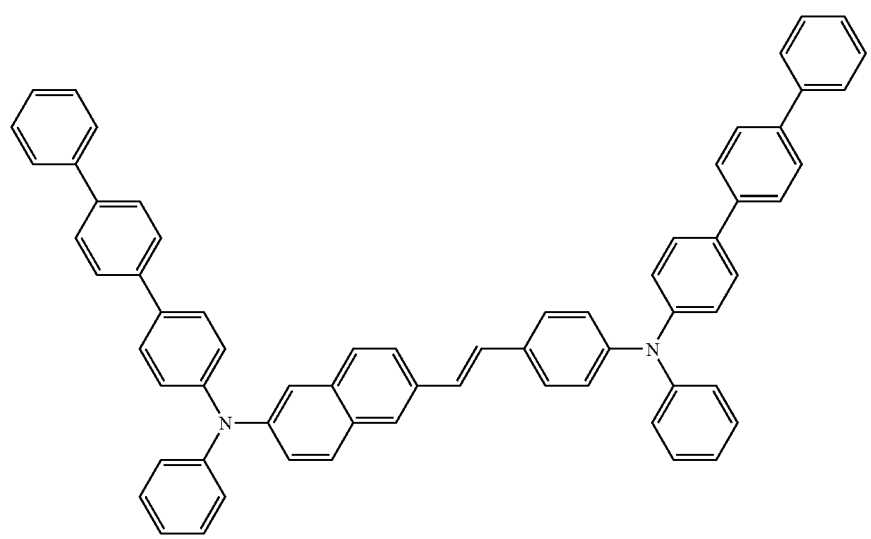
Ex-24
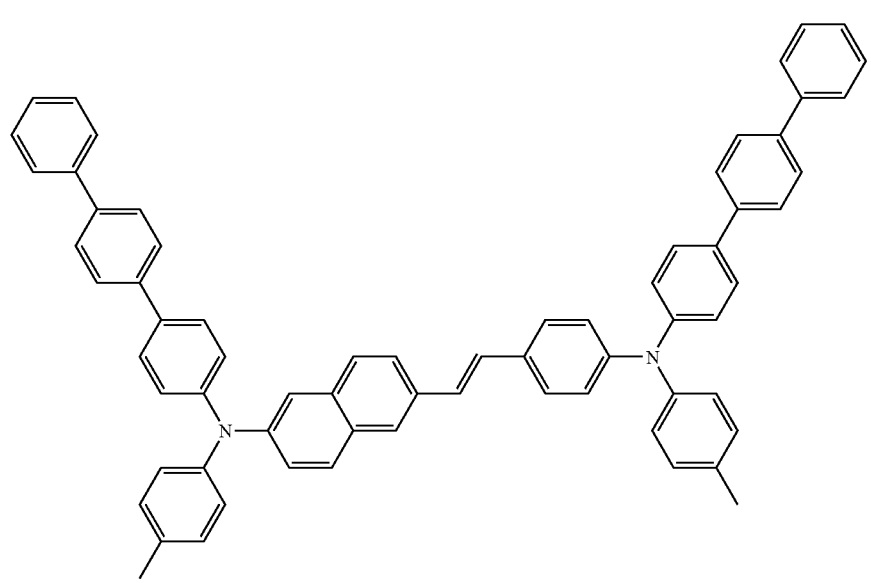

-continued
Ex-25
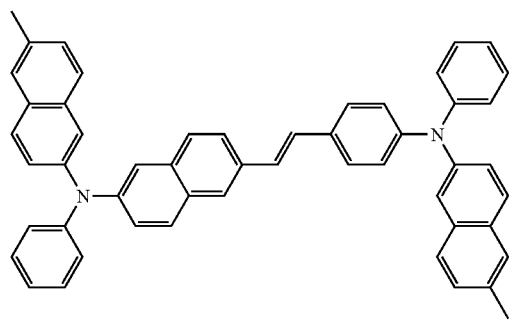
Ex-26
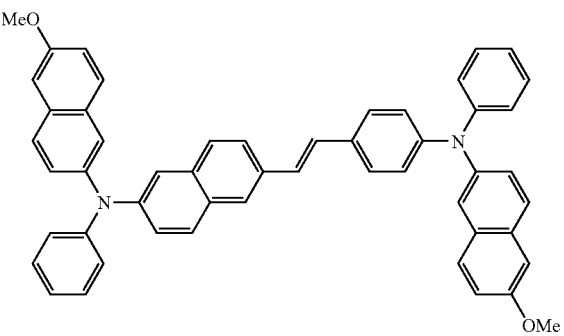
Ex-27
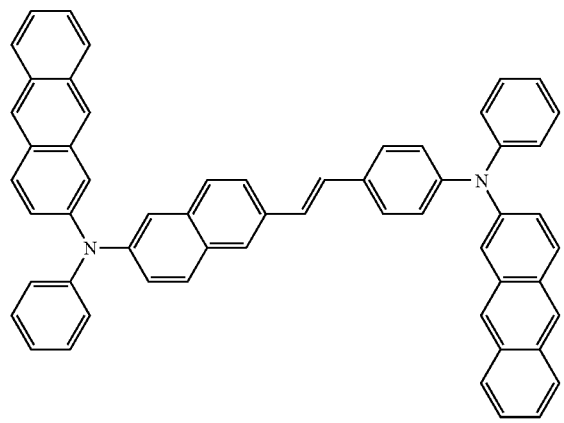
Ex-28
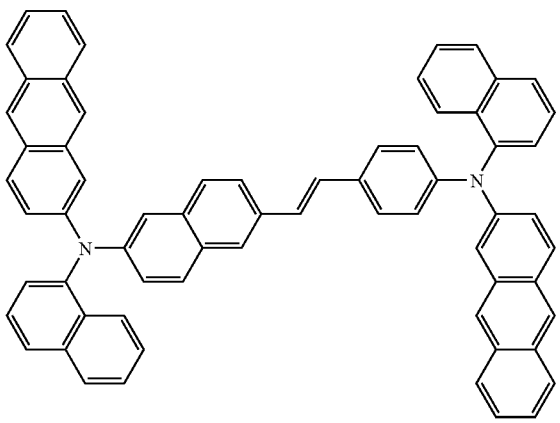
Ex-29
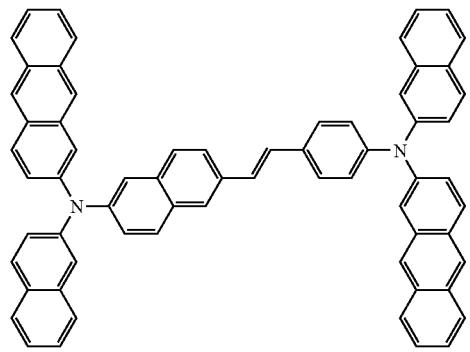
Ex-30
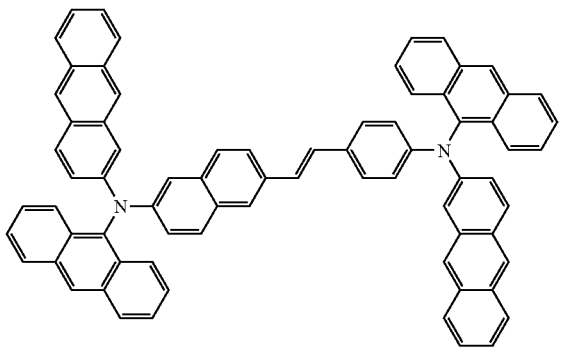
Ex-31
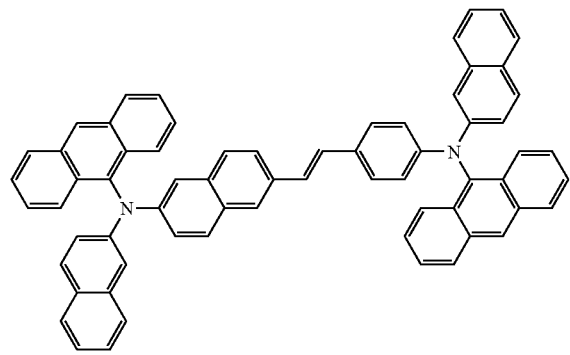
Ex-32
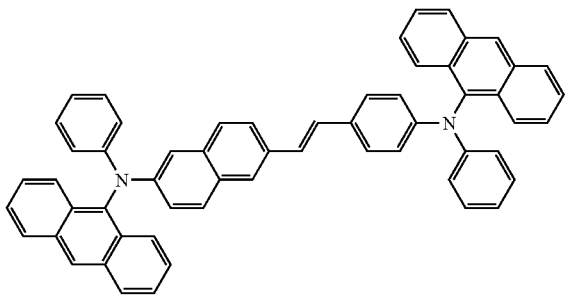

-continued
Ex-33
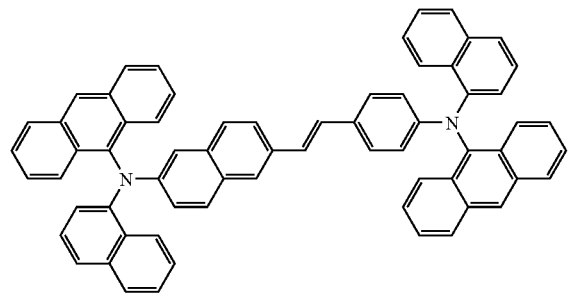
Ex-34
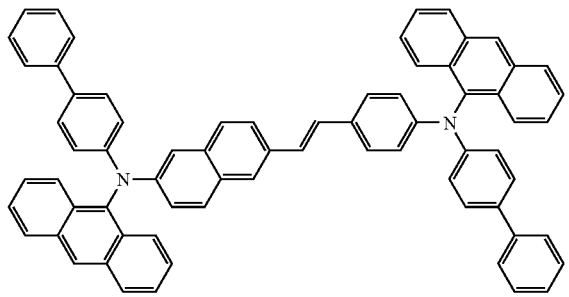
Ex-35
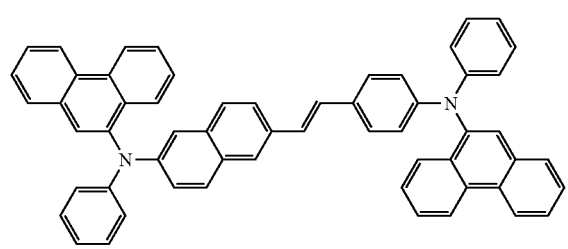
Ex-36
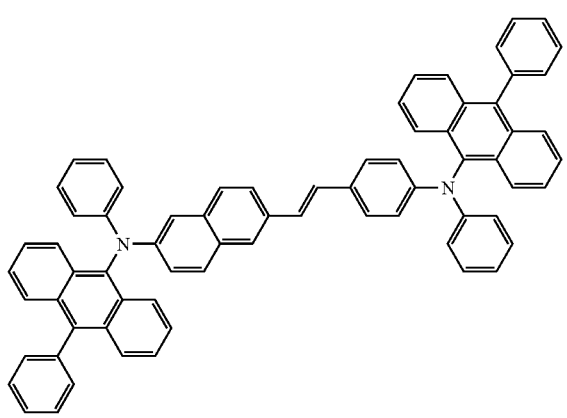
Ex-37
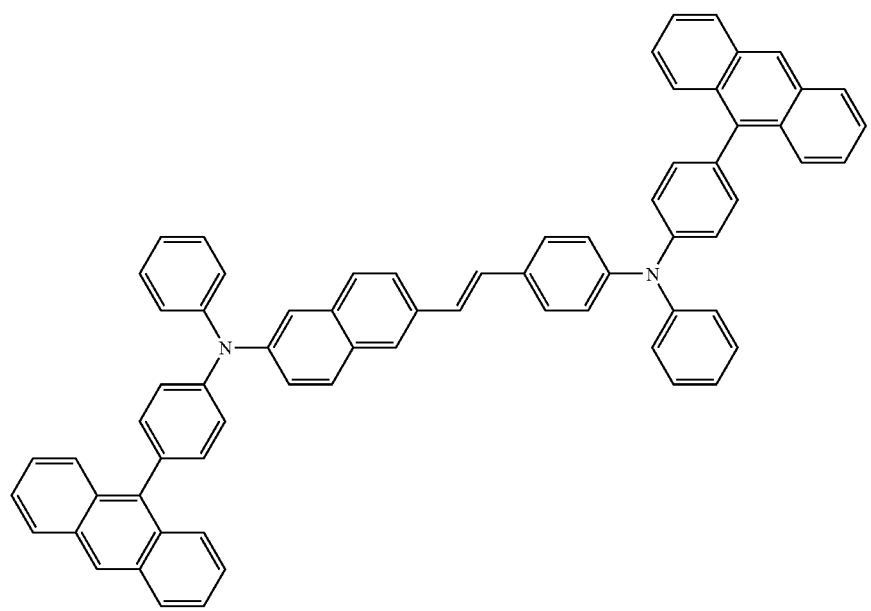

-continued
Ex-38
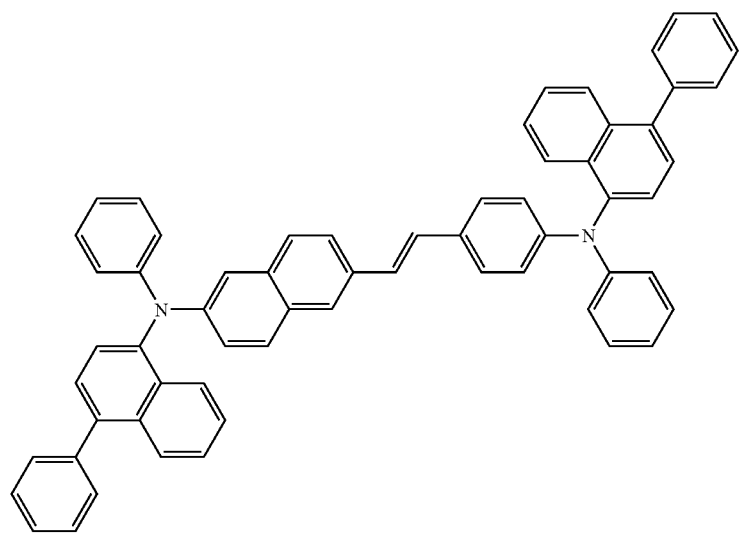
Ex-39
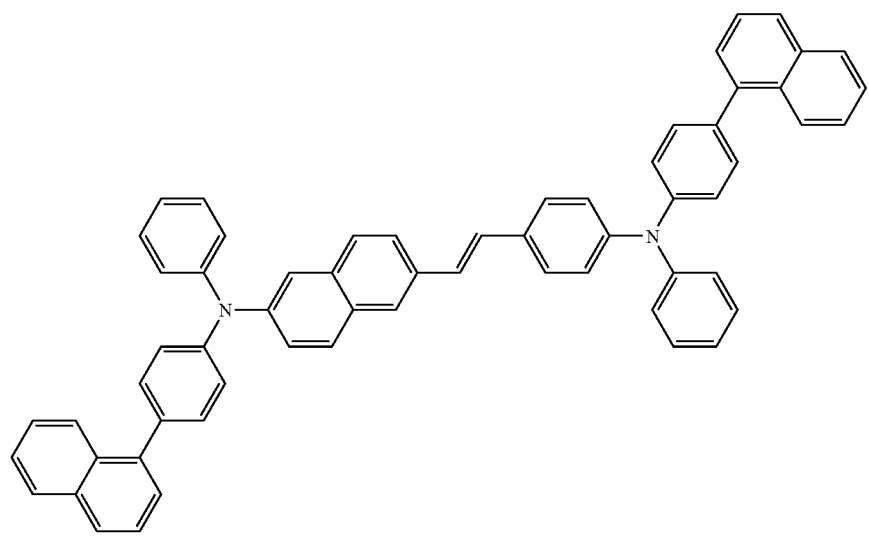
Ex-40
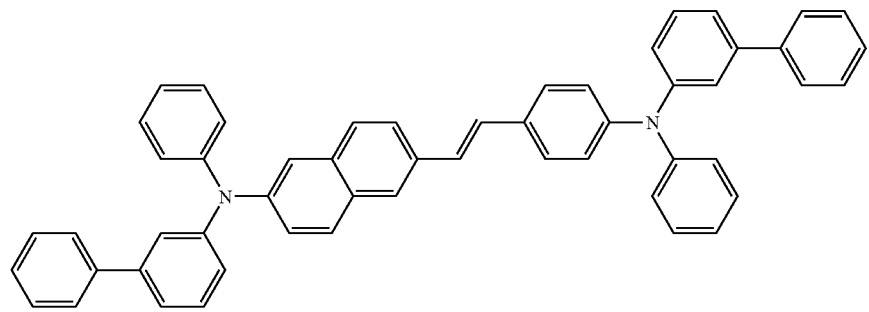

Ex-41
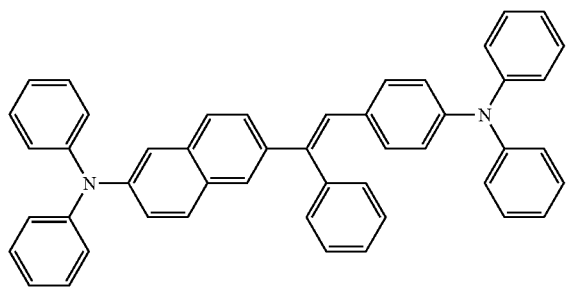

Ex-42
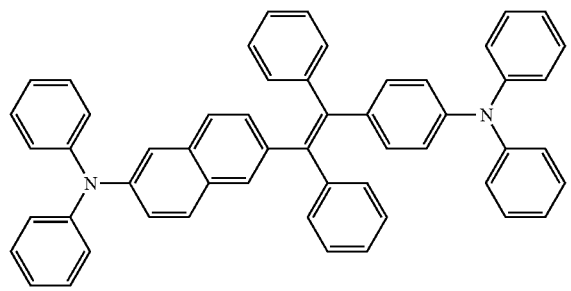

Ex-43
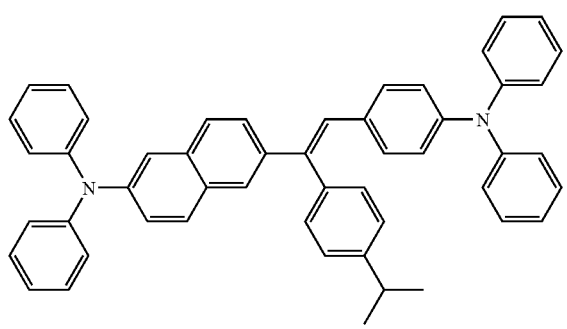

Ex-44
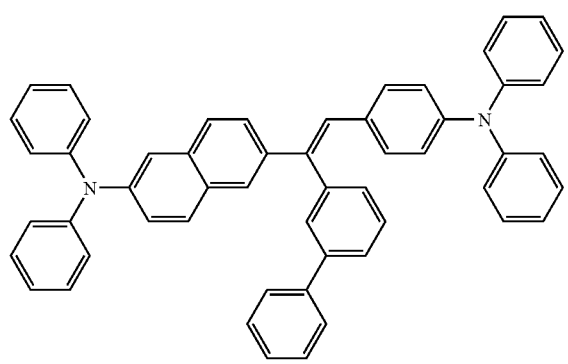

BEST MODE

Figure 1:
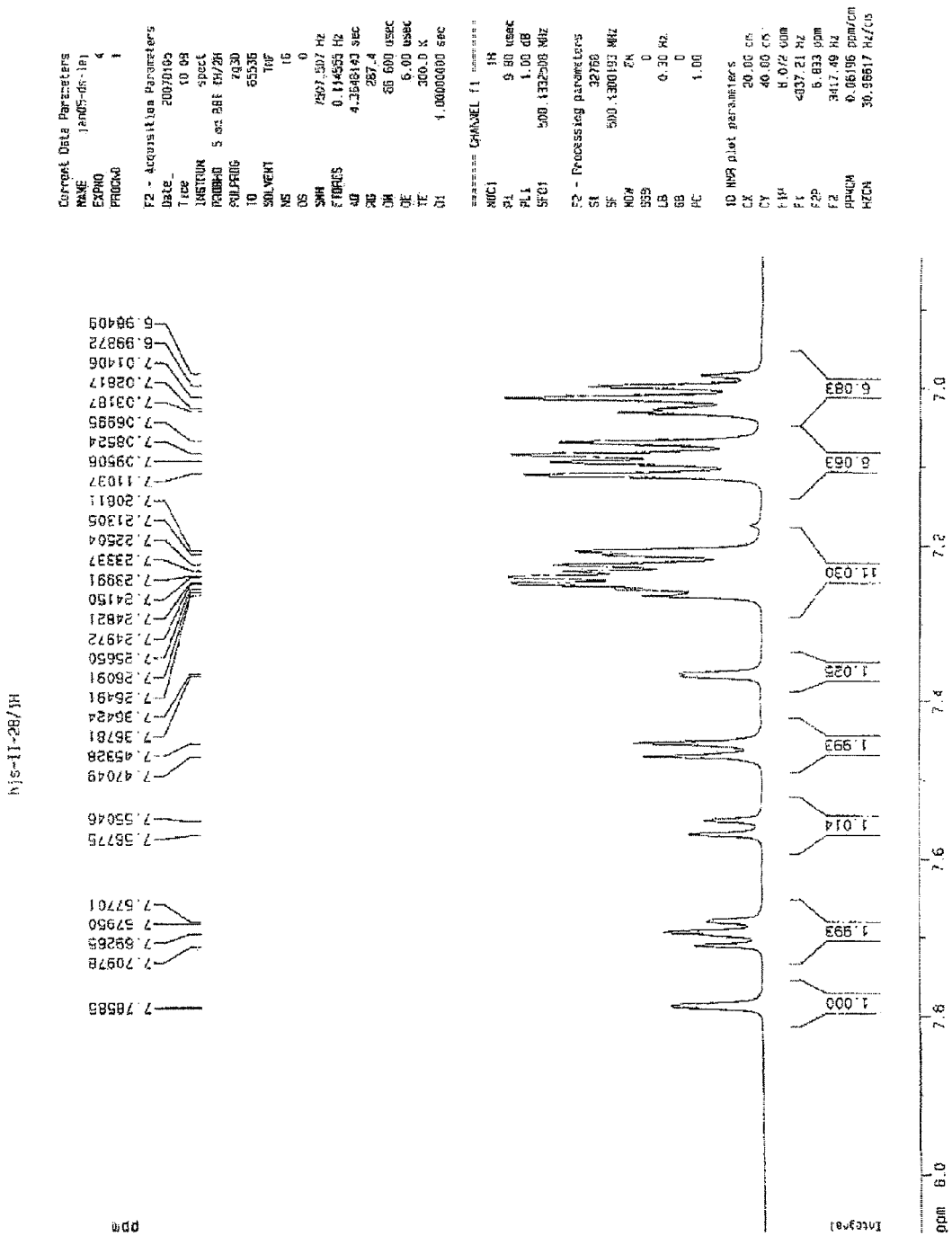
FIG. 1 is a diagram illustrating $^1$H-NMR data of Compound Ex-1 of the present invention.

Reference will now be made in detail to exemplary embodiments of the present invention. However, the following examples are illustrative merely, and the scope of the present invention is not limited thereto.

EXAMPLES

Preparation Example 1

Preparation of (6-bromonaphthalene-2-yl)methanol

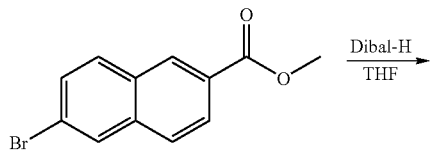

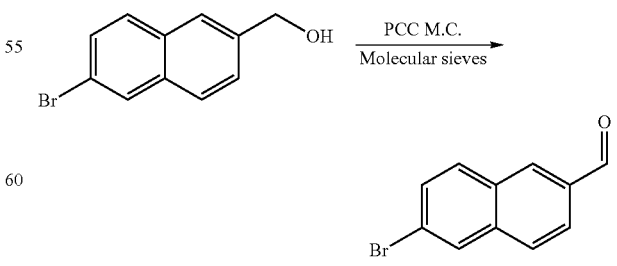

Methyl 6-bromo-2-naphthoate (5 g, 18.9 mmol) was dissolved in purified THF (100 mL) under a nitrogen atmosphere, the reaction solution was cooled down to 0° C., and then diisobutyl aluminum hydride (18.9 mL, 1.0M hexane solution) was added thereto. The reaction mixture solution was stirred at room temperature for 3 hours. Sodium bicarbonate (20 mL) was added to the reaction mixture solution, and then the solvent was removed by extraction with water and dichloromethane. The extracted material was dried in vacuum to thereby obtain a white solid (4.3 g, yield: 95%).

Preparation Example 2

Preparation of 6-bromo-2-naphthalenealdehyde

Pyridinium chlorochromate (7.8 g, 36.3 mmol), 4 Å molecular sieve (9.1 g), and purified dichloromethane (100 mL) were put into a reaction vessel under a nitrogen atmosphere, a solution prepared by dissolving (6-bromonaphthalene-2-yl)methanol (4.3 g, 18.1 mmol) in purified dichloromethane (100 mL) was slowly added thereto at 0° C. The reaction mixture solution was stirred at room temperature for 1 hour, and then was filtered using silica gel. After the solvent was removed, the filtered material was dried in vacuum to thereby obtain a white solid (4.0 g, yield: 94%).

Preparation Example 3

Preparation of diethyl 4-bromobenzylphosphonate

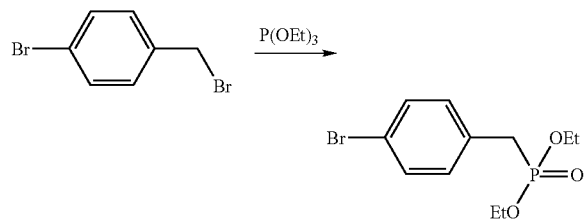

4-bromobenzylbromide (10.0 g, 40.0 mmol) was dissolved in triethylphosphite (8.4 mL, 48.0 mmol) under a nitrogen atmosphere, and the reaction solution was refluxed and stirred for 24 hours. The reaction solution was passed through a silica gel column by using hexane-ethylacetate 7:3 as an eluant. After the solvent was removed, the residue material was dried in vacuum to thereby obtain pale yellow oil (10.0 g, yield: 81%).

Preparation Example 4

Preparation of (E)-2-bromo-6-(4-bromostyryl)naphthalene

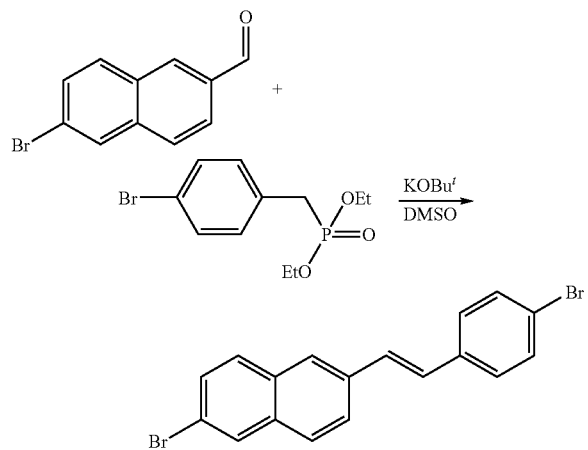

6-bromo-2-naphthaldehyde (4.0 g, 17.1 mmol) and diethyl-4-bromobenzylphosphonate (6.3 g, 20.5 mmol) were dissolved in purified dimethylsulfoxide (100 mL) under a nitrogen atmosphere, the reaction solution was cooled down to 0° C., and then potassium t-butoxide (2.5 g, 20.5 mmol) was slowly added thereto. The reaction mixture solution was stirred at room temperature for 12 hours. The reaction mixture solution was subjected to extraction with water and dichloromethane to thereby remove the solvent. The extracted material was sufficiently washed with methanol, and was dried in vacuum to thereby obtain a white solid (6.0 g, yield: 91%).

Preparation Example 5

Preparation of (4-(diphenylamino)phenyl)(phenyl)methanone

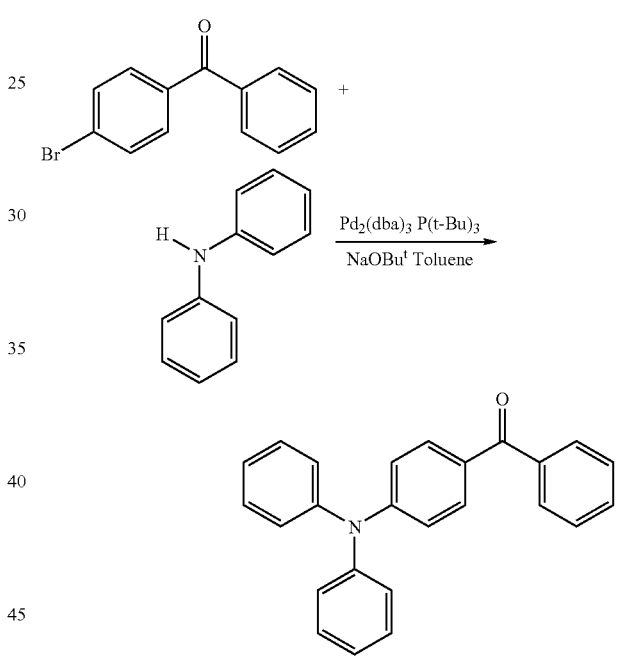

(4-bromophenyl)(phenyl)methanone (5.0 g, 19.2 mmol) and diphenylamine (4.2 g, 25.0 mmol) were dissolved in 150 mL of toluene under a nitrogen atmosphere, and then tris (benzylidene acetone) dipalladium (0.4 g, 0.4 mmol) was added thereto under nitrogen. Also, P(t-Bu)$_3$ (0.8 g, 3.8 mmol) was added to the reaction mixture solution, followed by addition of NaOBu$^t$ (5.5 g, 57.7 mmol). The reaction mixture solution was refluxed and stirred for 24 hours. After the reaction was over, the reaction mixture solution was filtered through a thin silica pad at a high temperature to thereby remove palladium. The filtrate was concentrated, and passed through a silica gel column by using hexane-dichloromethane 7:3 as an eluant. After the solvent was removed, the residue material was dried in vacuum to thereby obtain a white solid (5.6 g, yield: 84%).

Preparation Example 6

Preparation of 4-benzyl-N,N-diphenylaniline

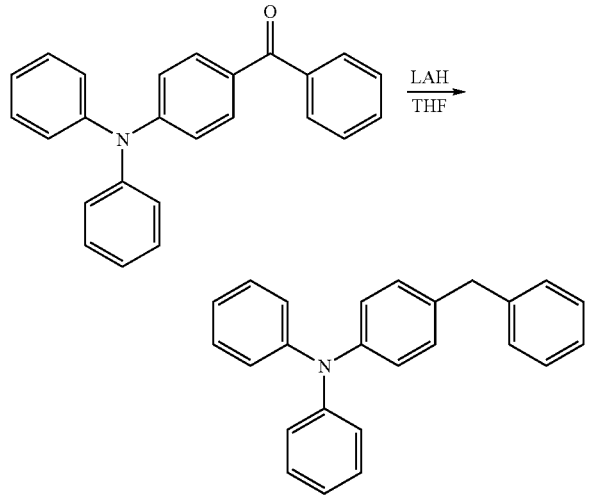

Lithium aluminum hydride (1.6 g, 43.0 mmol) was dissolved in purified tetrahydrofuran (30 mL) under a nitrogen atmosphere, and the reaction solution was stirred. A solution prepared by dissolving (4-(diphenylamino)phenyl) (phenyl) methanone (5.0 g, 14.3 mmol) in purified tetrahydrofuran (100 mL) was slowly added thereto at 0° C. The reaction mixture solution was stirred at room temperature for 2 hours, and then distilled water (30 mL) was added to the reaction mixture solution, followed by addition of aqueous sodium hydroxide solution (100 mL). The reaction solution was subjected to extraction with dichloromethane, the solvent was removed from the extracted material, and then the residue material was dried in vacuum to thereby obtain a white solid (4.1 g, yield: 86%).

Preparation Example 7

Preparation of N,N-diphenyl-4-(phenyl(trimethylsilyl)methyl)aniline

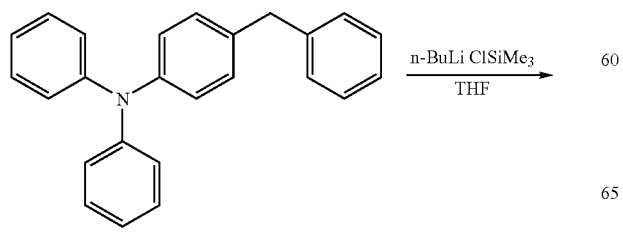

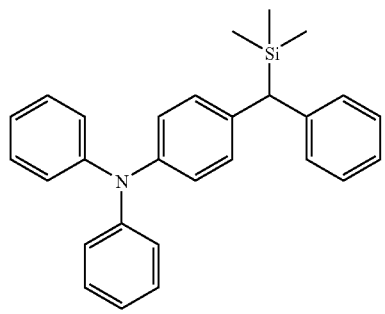

4-benzyl-N,N-diphenylaniline (5.0 g, 14.9 mmol) was dissolved in tetrahydrofuran (80 mL) under a nitrogen atmosphere. n-Butyllithium (10.3 mL, 16.4 mmol) was slowly added to the reaction solution at −78° C., and then the reaction mixture solution was stirred at room temperature for 1 hour. Also, the reaction mixture solution with chlorotrimethylsilane (1.8 g, 16.4 mmol) added thereto was stirred at room temperature for 1 hour. The reaction mixture solution was passed through a silica gel column by using hexane as an eluant. After the solvent is removed, the residue material was dried in vacuum to thereby a white solid (5.1 g, yield: 84%).

Preparation Example 8

Preparation of (E)-4-(2-(6-bromonaphthalene-2-yl)-1-phenylvinyl)-N,N-diphenylaniline

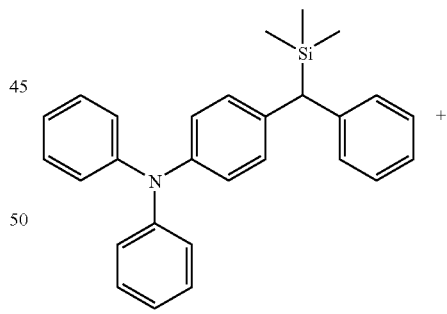

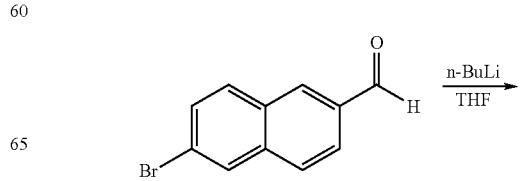

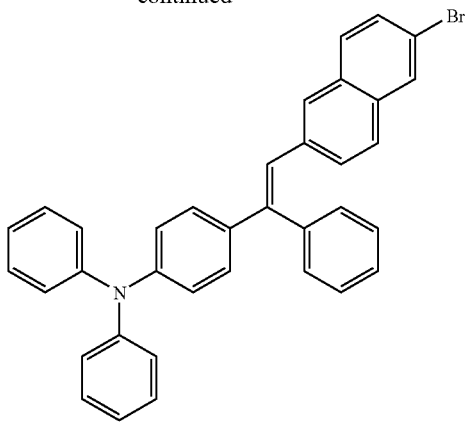

N,N-diphenyl-4-(phenyl(trimethylsilyl)methyl) aniline (5.0 g, 12.3 mmol) was dissolved in purified tetrahydrofuran (30 mL) under a nitrogen atmosphere, and n-butyllithium (8.4 mL, 13.5 mmol) was slowly added thereto at −78° C. The reaction mixture solution was stirred at room temperature for 8 hours. 6-bromo-2-naphthaldehyde (2.9 g, 12.3 mmol) dissolved in tetrahydrofuran (10 mL) was added thereto at room temperature. The reaction mixture solution was stirred at room temperature for 24 hours. The reaction mixture solution was subjected to extraction with dichloromethane and distilled water, and the extracted material is subjected to column chromatography (hexane:dichloromethane=9:1). The reaction solvent was removed, and then the residue material was dried in vacuum to thereby obtain a pale yellow solid (4.5 g, yield: 66%).

Preparation Example 9

Preparation of (4-chlorophenyl)(4-isopropylphenyl)methanone

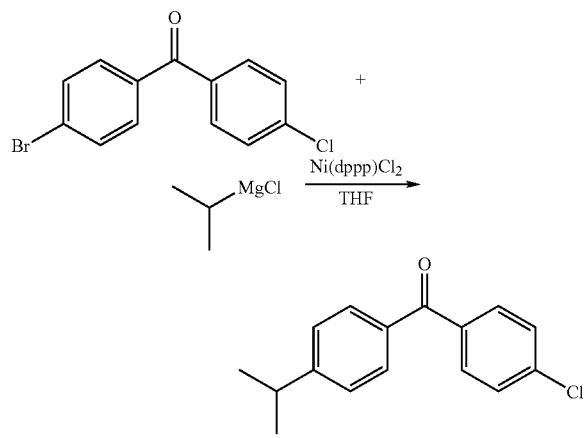

(4-bromophenyl)(4-chlorophenyl)methanone (10.0 g, 12.3 mmol) and bis(diphenylphosphino)propane nickel(II) chloride (0.4 g, 0.7 mmol) were dissolved in purified tetrahydrofuran (200 mL) under a nitrogen atmosphere, and isopropyl magnesium chloride (18.7 mL, 37.4 mmol) was slowly added thereto at 0° C. The reaction mixture solution was stirred at room temperature for 24 hours. The reaction mixture solution was subjected to extraction with dichloromethane and distilled water, and the extracted material was subjected to column chromatography (hexane:ethylacetate=8:2). The reaction solvent was removed, and then the residue material was dried in vacuum to thereby obtain a white solid (6.3 g, yield: 72%).

Preparation Example 10

Preparation of biphenyl-3-yl(4-(diphenylamino)phenyl)methanone

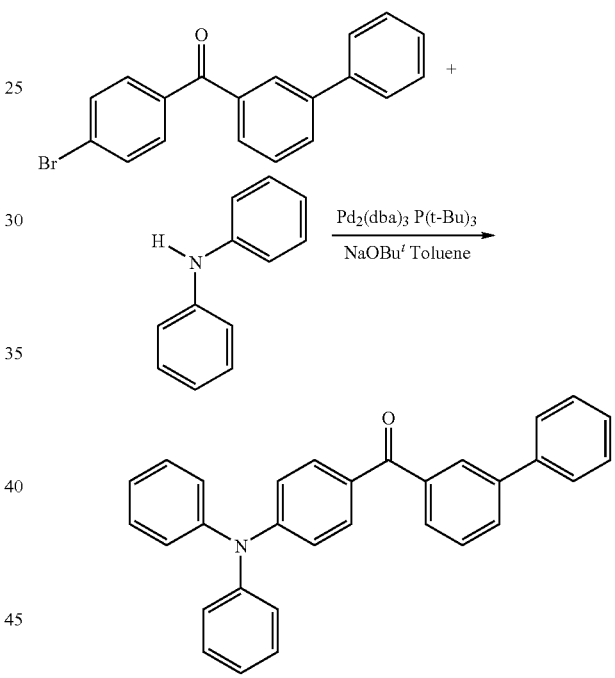

Biphenyl-3-yl(4-bromophenyl)methanone (5.0 g, 14.83 mmol) and diphenylamine (3.8 g, 22.2 mmol) were dissolved in toluene (150 mL) under a nitrogen atmosphere, and then tris(benzylidine acetone dipalladium) (0.3 g, 0.3 mmol) was added thereto under nitrogen. Also, P(t-Bu)$_3$ (0.3 g, 1.5 mmol) was added to the reaction mixture solution, followed by addition of NaOBu$^t$ (4.3 g, 44.5 mmol). The reaction mixture solution was refluxed and stirred for 24 hours. After the reaction was over, the reaction mixture solution was filtered through a thin silica pad at a high temperature to thereby remove palladium. The filtrate was concentrated, and was passed through a silica gel column by using hexane-dichloromethane 7:3 as an eluant. After the solvent was removed, the residue material was dried in vacuum to thereby obtain a white solid (5.1 g, yield: 81%).

Example 1

Preparation of Compound Ex-1

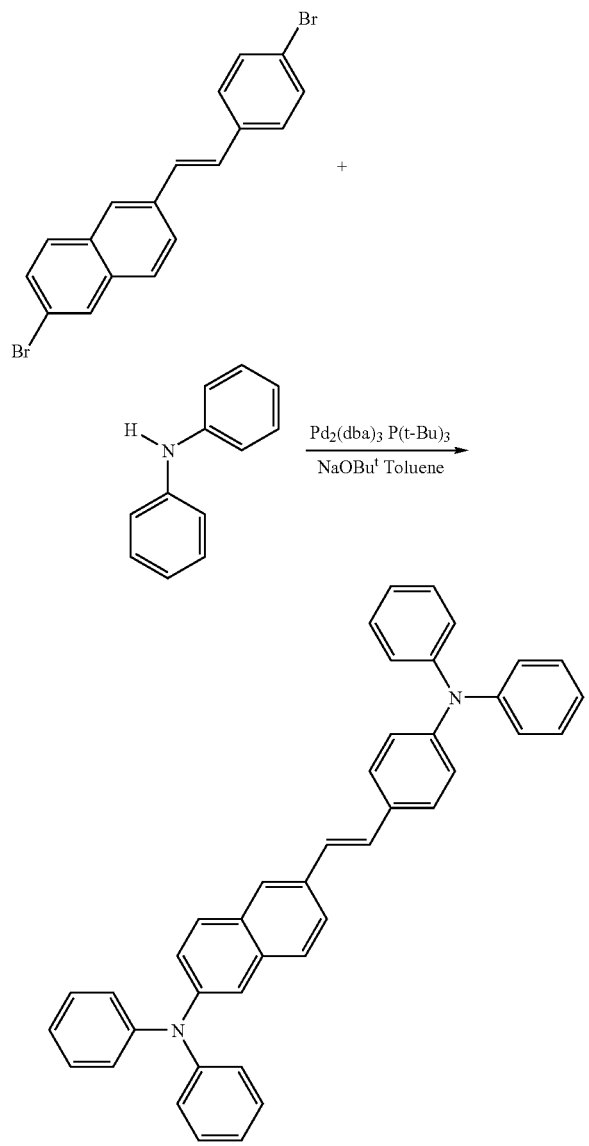

2-bromo-6-(4-bromostyryl)naphthalene (3.5 g, 9.0 mmol) and diphenylamine (3.8 g, 22.6 mmol) were dissolved in toluene (70 mL) under a nitrogen atmosphere, and then tris (benzylidine acetone dipalladium) (0.4 g, 0.5 mmol) was added thereto under nitrogen. Also, P(t-Bu)$_3$ (0.2 g, 0.9 mmol) was added to the reaction mixture solution, followed by addition of NaOBu$^t$ (2.6 g, 27.1 mmol). The reaction mixture solution was refluxed and stirred for 24 hours. After the reaction was over, the reaction mixture solution was filtered through a thin silica pad at a high temperature to thereby remove palladium. The filtrate was concentrated, and was passed through a silica gel column by using hexane-dichloromethane 7:3 as an eluant. After the solvent was removed, the residue material was dried in vacuum to thereby obtain a yellow green solid (4.5 g, yield: 88%).

$^1$H-NMR of Compound Ex-1 was as illustrated in FIG. 1, and its element analysis resulted in the following composition: Calcd. C, 89.33; H, 5.71; N, 4.96. Anal. C, 89.52; H, 5.53; N, 4.90. Also, as a result of mass analysis, a molecular weight peak was observed at 564 (M$^+$).

Example 2

Preparation of Compound Ex-10

Figure 2:
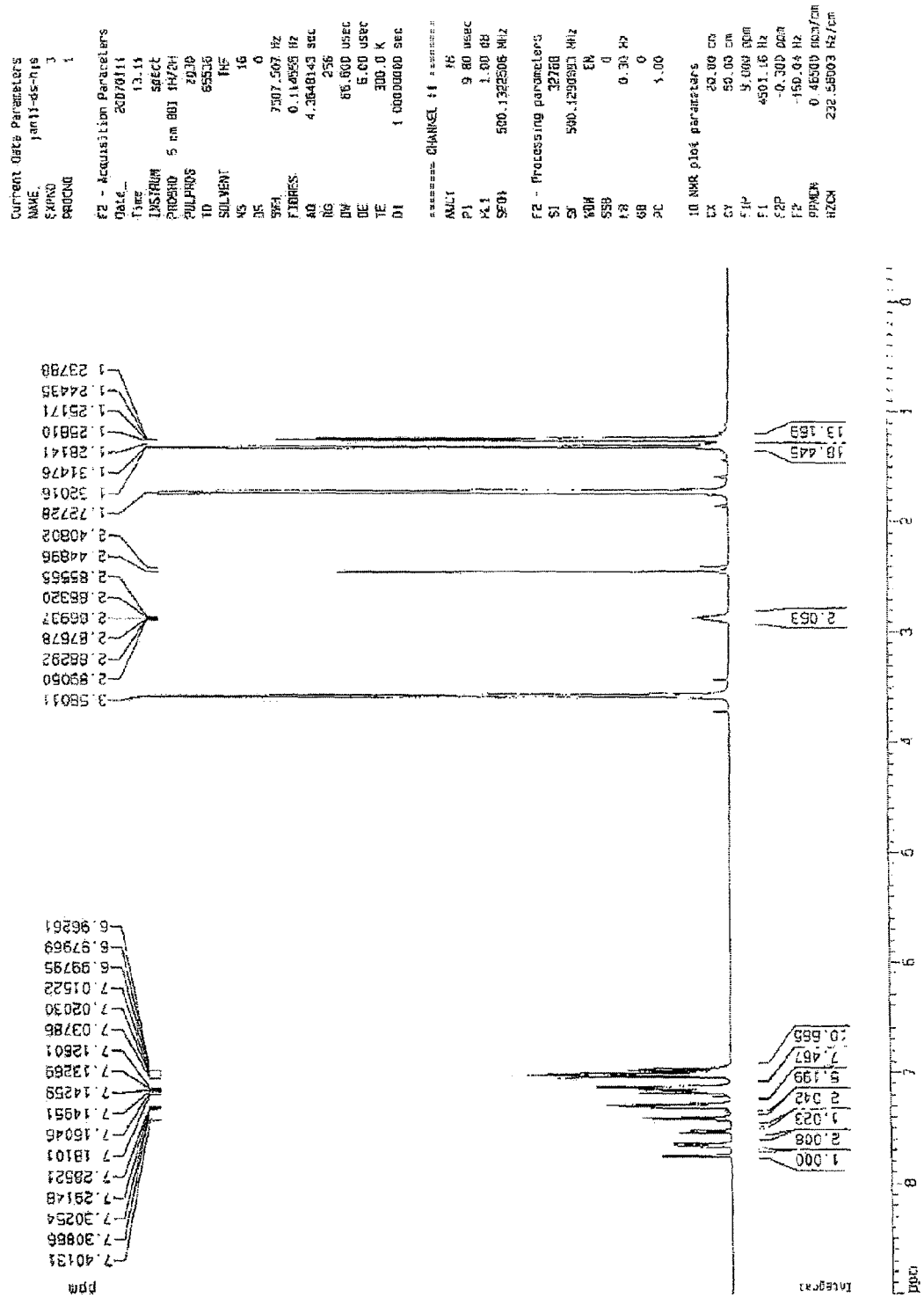
FIG. 2 is a diagram illustrating $^1$H-NMR data of Compound Ex-10 of the present invention.

Compound Ex-10 was obtained by carrying out reaction between (E)-2-bromo-6-(4-bromostyryl)naphthalene, prepared in Preparation Example 4, and 4-t-butyl-N-(4-isopropylphenyl)benzene amine in the same manner as in Example 1. $^1$H-NMR of Compound Ex-10 was as illustrated in FIG. 2, and its element analysis resulted in the following composition: Calcd. C, 88.37; H, 7.95; N, 3.68. Anal. C, 89.01; H, 7.79; N, 3.63.

Example 3

Preparation of Compound Ex-14

Figure 3:
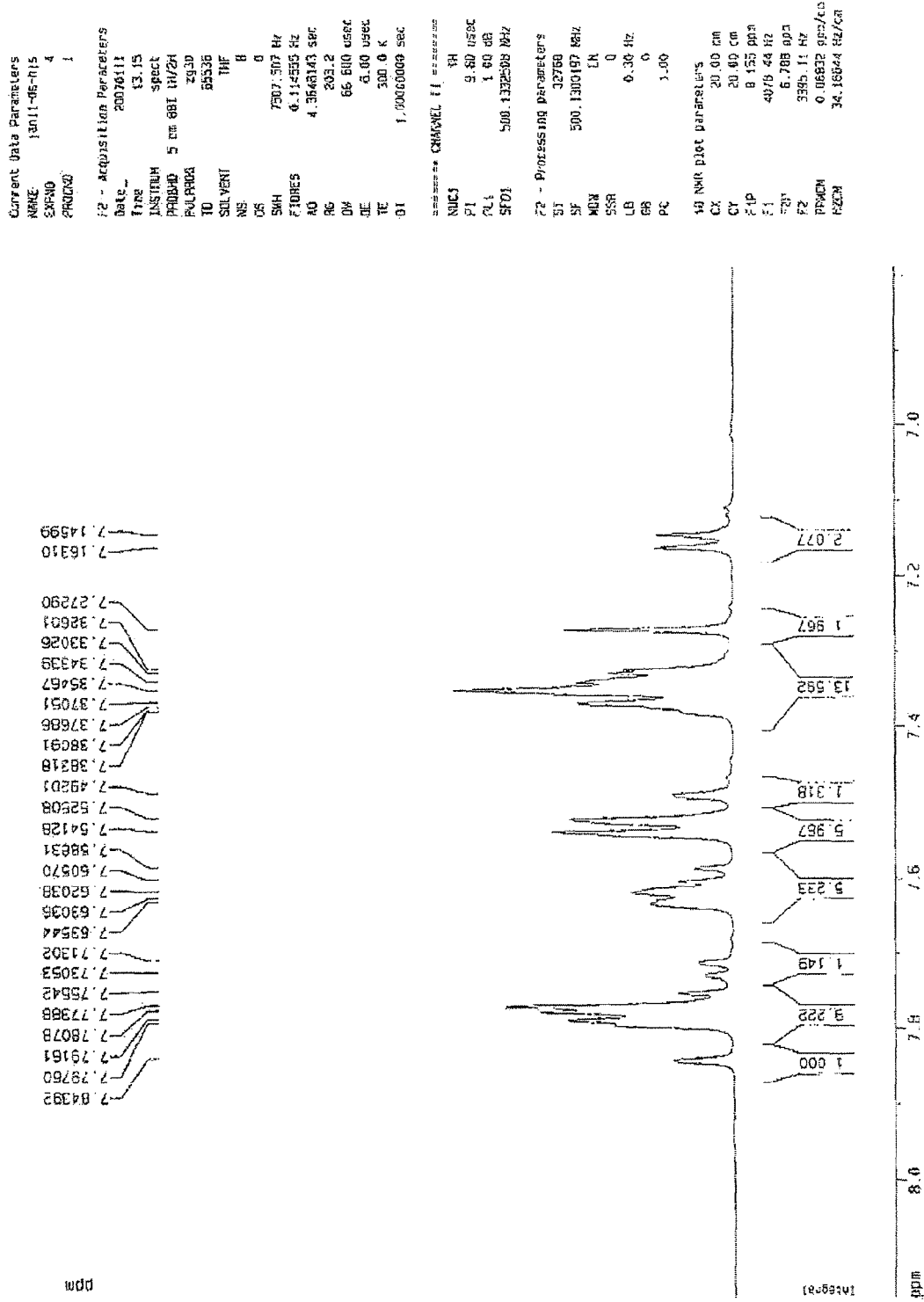
FIG. 3 is a diagram illustrating $^1$H-NMR data of Compound Ex-14 of the present invention.

Compound Ex-14 was obtained by carrying out reaction between (E)-2-bromo-6-(4-bromostyryl)naphthalene, prepared in Preparation Example 4, and dinaphthalene-2-ylamine in the same manner as in Example 1. $^1$H-NMR of Compound Ex-14 was as illustrated in FIG. 3, and its element analysis resulted in the following composition: Calcd. C, 91.07; H, 5.27; N, 3.66., Anal. C, 90.56; H, 5.44; N, 3.78.

Example 4

Preparation of Compound Ex-21

Figure 4:
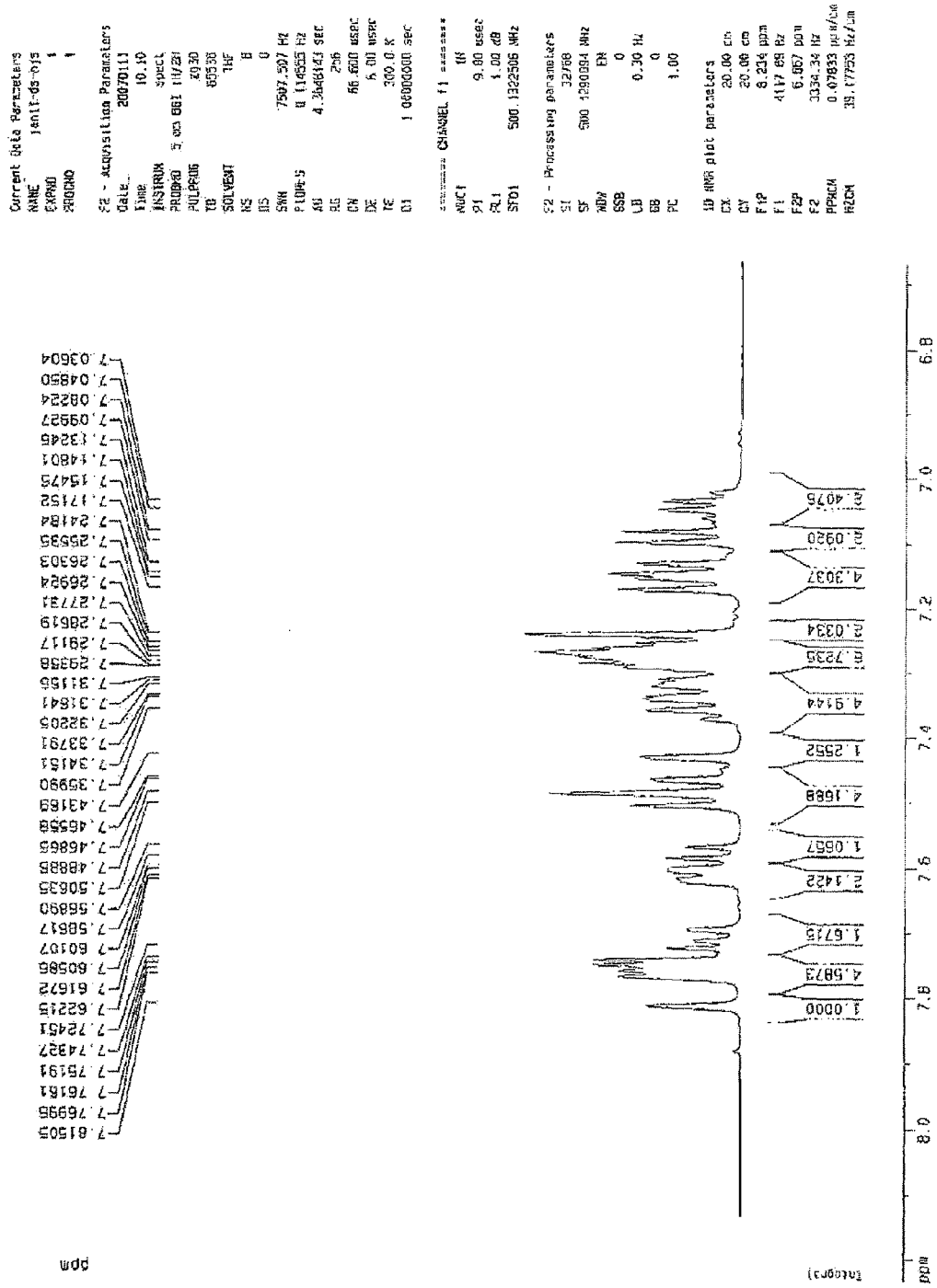
FIG. 4 is a diagram illustrating $^1$H-NMR data of Compound Ex-21 of the present invention.

Compound Ex-21 was obtained by carrying out reaction between (E)-2-bromo-6-(4-bromostyryl)naphthalene, prepared in Preparation Example 4, and N-phenyl-naphthalene-1-amine in the same manner as in Example 1. $^1$H-NMR of Compound Ex-21 was as illustrated in FIG. 4, and its element analysis resulted in the following composition: Calcd. C, 90.33; H, 5.46; N, 4.21., Anal. C, 90.78; H, 5.45; N, 4.09.

Example 5

Preparation of Compound Ex-41

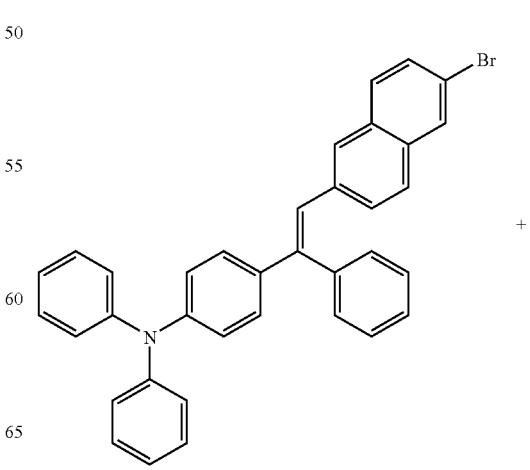

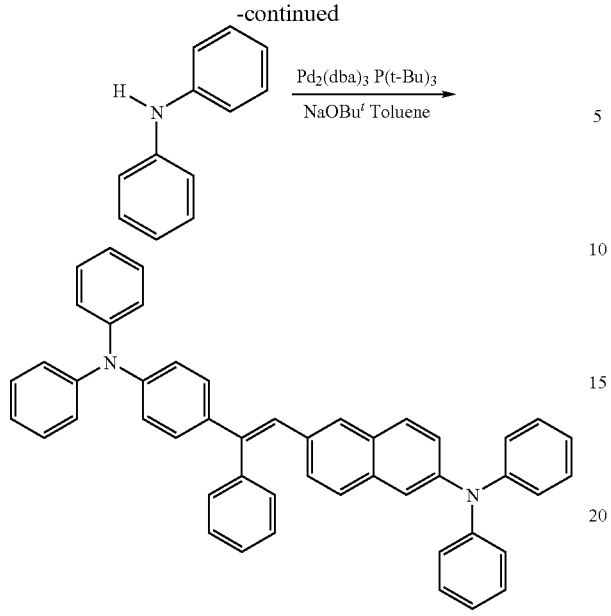

(E)-4-(2-(6-bromonaphthalene-2-yl)-1-phenylvinyl)-N,N-diphenylaniline (5.0 g, 9.1 mmol) and diphenylamine (2.0 g, 11.8 mmol) were dissolved in toluene (80 mL) under a nitrogen atmosphere, and then tris(benzylidine acetone dipalladium) (0.2 g, 0.2 mmol) was added thereto under nitrogen. Also, P(t-Bu)$_3$ (0.4 g, 1.8 mmol) was added to the reaction mixture solution, followed by addition of NaOBu$^t$ (2.6 g, 27.2 mmol). The reaction mixture solution was refluxed and stirred for 24 hours. After the reaction was over, the reaction mixture solution was filtered through a thin silica pad at a high temperature to thereby remove palladium. The filtrate was concentrated, and was passed through a silica gel column by using hexane-dichloromethane 7:3 as an eluant. After the solvent was removed, the residue material was dried in vacuum to thereby obtain a pale yellow solid (5.3 g, yield: 91%).

$^1$H-NMR (THF) of Compound Ex-41 was as follows: 7.9 (s, 1H), 7.8 (t, 2H), 7.6 (d, 1H), 7.5 (d, 2H), 7.2 (m, 16H), 6.8 (dd, 8H), 6.6 (dd, 6H). Element analysis for Compound Ex-41 resulted in the following composition: Calcd. C, 89.97; H, 5.66; N, 4.37. Anal. C, 89.72; H, 5.71; N, 4.57. Also, as a result of mass analysis, a molecular weight peak was observed at 640 (M$^+$).

Example 6

Preparation of Compound Ex-42

A (6-bromonaphthalene-2-yl)-1,2-(diphenylvinyl)-N,N-diphenylaniline compound was prepared by carrying out reaction between N,N-diphenyl-4-(phenyl(trimethylsilyl)methyl)aniline, prepared in Preparation Example 7, and (6-bromonaphthalene-2-yl) (phenyl)methanone in the same manner as in Preparation Example 8 Compound Ex-42 was obtained by carrying out reaction of (6-bromonaphthalene-2-yl)-1,2-(diphenylvinyl)-N,N-diphenylaniline obtained in Preparation Example 8 in the same manner as in Example 5.

$^1$H-NMR (THF) of Compound Ex-42 was as follows: 7.8 (dd, 3H), 7.6 (d, 2H), 7.4 (m, 21H), 7.0 (dd, 8H), 6.8 (dd, 6H). Element analysis for Compound Ex-42 resulted in the following composition: Calcd. C, 90.47; H, 5.62; N, 3.91. Anal. C, 90.62; H, 5.44; N, 3.94.

Example 7

Preparation of Compound Ex-43

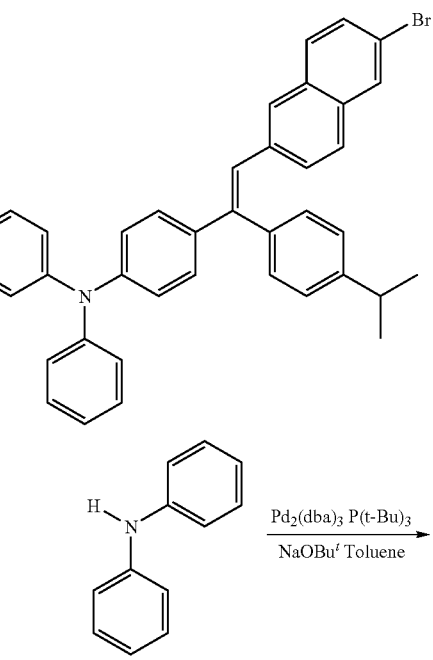

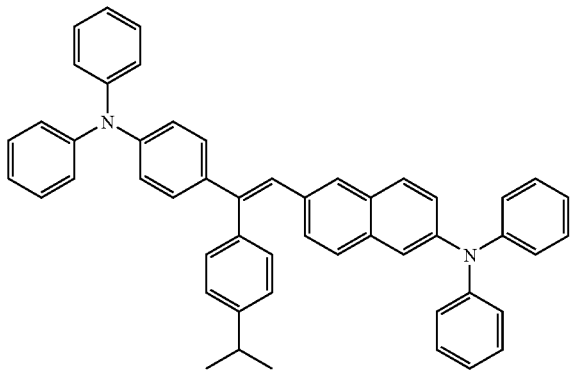

(E)-4-(2-(6-bromonaphthalene-2-yl)-1-(4-isopropylphenyl)vinyl)-N,N-diphenylaniline (5.0 g, 8.4 mmol) and diphenylamine (2.1 g, 12.6 mmol) were dissolved in toluene (100 mL) under a nitrogen atmosphere, and then tris(benzylidine acetone dipalladium) (0.2 g, 0.2 mmol) was added thereto under nitrogen. Also, P(t-Bu)$_3$ (0.2 g, 0.8 mmol) was added to the reaction mixture solution, followed by addition of NaOBu$^t$ (2.4 g, 25.3 mmol). The reaction mixture solution was refluxed and stirred for 24 hours. After the reaction was over, the reaction mixture solution was filtered through a thin silica pad at a high temperature to thereby remove palladium. The filtrate was concentrated, and was passed through a silica gel column by using hexane-dichloromethane 7:3 as an eluant. After the solvent was removed, the residue material was dried in vacuum to thereby obtain a pale yellow solid (5.4 g, yield: 94%).

$^1$H-NMR (THF) of Compound Ex-43 was as follows: 1.3 (s, 6H), 3.0 (t, 1H), 8.0 (s, 1H), 7.8 (t, 2H), 7.7 (d, 2H), 7.4 (m, 16H), 7.0 (dd, 8H), 6.8 (dd, 6H). Element analysis for Compound Ex-43 resulted in the following composition: Calcd. C, 89.70; H, 6.20; N, 4.10. Anal. C, 89.83; H, 6.14; N, 4.03. Also, as a result of mass analysis, a molecular weight peak was observed at 682 (M$^+$).

Example 8

Preparation of Compound Ex-44

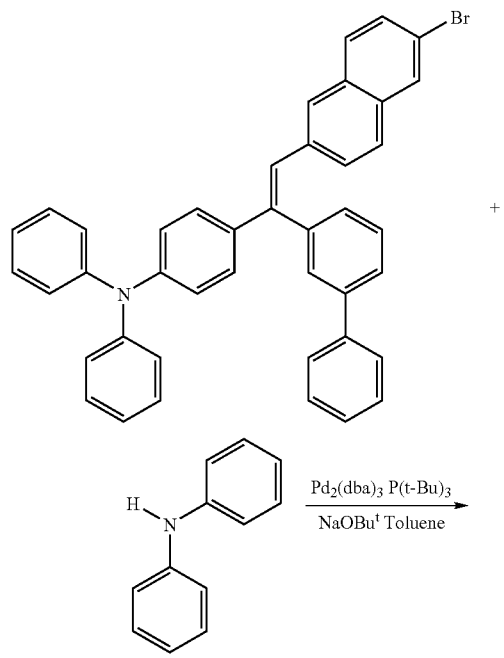

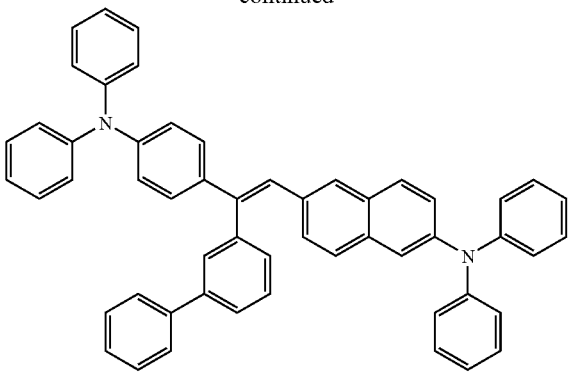

(Z)-4-(1-(biphenyl-3-yl)-2-(6-bromonaphthalene-2-yl)vinyl)-N,N-diphenylaniline (7.0 g, 11.2 mmol) and diphenylamine (2.8 g, 16.7 mmol) were dissolved in toluene (200 mL) under a nitrogen atmosphere, and then tris(benzylidine acetone dipalladium) (0.2 g, 0.2 mmol) was added thereto under nitrogen. Also, P(t-Bu)$_3$ (0.2 g, 1.1 mmol) was added to the reaction mixture solution, followed by addition of NaOBu$^t$ (3.2 g, 33.5 mmol). The reaction mixture solution was refluxed and stirred for 24 hours. After the reaction was over, the reaction mixture solution was filtered through a thin silica pad at a high temperature to thereby remove palladium. The filtrate was concentrated, and was passed through a silica gel column by using hexane-dichloromethane 7:3 as an eluant. After the solvent was removed, the residue material was dried in vacuum to thereby obtain a pale yellow solid (7.6 g, yield: 95%).

$^1$H-NMR (THF) of Compound Ex-44 was as follows: 8.0 (d, 1H), 7.8 (m, 12H), 7.5 (d, 2H), 7.3 (m, 12H), 7.0 (d, 1H), 6.9 (t, 2H), 6.7 (m, 10H). Element analysis for Compound Ex-44 resulted in the following composition: Calcd. C, 90.47; H, 5.62; N, 3.91. Anal. C, 90.35; H, 5.71; N, 3.94. Also, as a result of mass analysis, a molecular weight peak was observed at 716 (M$^+$).

Examples 9 to 30

Fabrication of Blue OLEDs

Compounds Ex-1, Ex-2, Ex-3, Ex-6, Ex-8, Ex-10, Ex-14, Ex-15, Ex-16, Ex-17, Ex-18, Ex-19, Ex-20, Ex-21, Ex-29, Ex-35, Ex-39, Ex-40, Ex-41, Ex-42, Ex-43, and Ex-44 of the present invention were prepared in the same manner as in the above examples, and blue OLEDs, each comprising each of the compounds as a dopant, were fabricated.

The resultant structures and characteristics of the devices are summarized in Tables 1 and 2.

TABLE 1

|  | HIL | HTL | EML | ETL | EIL | Cathode |
|---|---|---|---|---|---|---|
| Material | DS-205 | NPB | Host + DS-405 (DOPANT) | Alq3 | LiF | Al |
| Thickness/Å | 600 | 150 | 285 + 15 | 250 | 10 | 2,000 |
| Evapo. Temp./° C. | 360~370 | 230~240 | HOST: 240~250 DOPANT: 170~180 | 240~250 | — | — |

DS-205 (arylamine derivative) with a thickness of 600 Å, commercially available from Doosan Corp., was used as a hole injecting layer (HIL), and NPB with a thickness of 150 Å was used as a hole transporting layer (HTL). Also, the AN7 compound disclosed in US Patent Laid-Open No. 2006/0043858 was used as a host, and each of Compounds Ex-1, Ex-2, Ex-3, Ex-6, Ex-8, Ex-10, Ex-14, Ex-15, Ex-16, Ex-17, Ex-18, Ex-19, Ex-20, Ex-21, Ex-29, Ex-35, Ex-39, Ex-40, Ex-41, Ex-42, Ex-43, and Ex-44 was used as a dopant. Each dopant was doped in an amount of 5%, an electron transporting layer (ETL) was formed of Alq3 with a thickness of 250 Å, and an electron injecting layer (EIL) was formed of LiF with a thickness of 10 Å.

Experimental Example

Evaluation on Characteristics of OLEDs of Examples 9 to 30

The characteristics of the devices fabricated in Examples 9 to 30 were evaluated at a current density of 10 mA/cm² to obtain the following results shown in Table 2:

TABLE 2

| Compound | Voltage (V) | CIE index (x, y) | Efficiency (cd/A) |
| --- | --- | --- | --- |
| Ex-1 | 4.7 | 0.153, 0.172 | 5.6 |
| Ex-2 | 4.9 | 0.155, 0.175 | 6.0 |
| Ex-3 | 4.6 | 0.160, 0.175 | 5.2 |
| Ex-6 | 5.2 | 0.159, 0.173 | 5.5 |
| Ex-8 | 5.0 | 0.150, 0.165 | 5.3 |
| Ex-10 | 5.3 | 0.163, 0.180 | 5.2 |
| Ex-14 | 5.2 | 0.158, 0.177 | 5.8 |
| Ex-15 | 5.1 | 0.155, 0.180 | 6.0 |
| Ex-16 | 5.3 | 0.155, 0.176 | 5.1 |
| Ex-17 | 5.5 | 0.159, 0.185 | 4.7 |
| Ex-18 | 5.1 | 0.162, 0.183 | 4.9 |
| Ex-19 | 5.4 | 0.157, 0.179 | 4.8 |
| Ex-20 | 4.9 | 0.158, 0.185 | 5.9 |
| Ex-21 | 5.1 | 0.166, 0.192 | 6.1 |
| Ex-29 | 5.6 | 0.175, 0.211 | 6.3 |
| Ex-35 | 5.8 | 0.177, 0.225 | 6.1 |
| Ex-39 | 6.3 | 0.166, 0.190 | 4.7 |
| Ex-40 | 4.9 | 0.158, 0.171 | 5.8 |
| Ex-41 | 5.2 | 0.157, 0.188 | 6.8 |
| Ex-42 | 5.3 | 0.158, 0.198 | 7.1 |
| Ex-43 | 5.5 | 0.167, 0.185 | 6.7 |
| Ex-44 | 5.7 | 0.159, 0.179 | 6.3 |

When an OLED was fabricated in the same manner as the OLED using the compound of the present invention, except that Compound 10 disclosed in US-A-2003-0044640 was used as a dopant, a driving voltage of 5.2V, CIE index 0.158, 0.182, and an efficiency of 5.0 cd/A were obtained. Therefore, it can be noted that the inventive compounds, such as Ex-1, Ex-2, etc., are more excellent in color purity (CIE index) and efficiency than the compound of the above US patent. Also, even when an aryl group substituent, such as Ex-41, Ex-42, Ex-43, and Ex-44, is used, equivalent effect can be obtained.

Industrial Applicability

As can be seen from the foregoing, asymmetric styryl derivatives and an OLED prepared using the same according to the present invention can provide a blue OLED with superior thermal stability, as well as improved luminous efficiency, improved brightness, and extended lifetime, by synthesizing a novel thermally stable compound with a styryl structure represented by Formula 1 of the present invention, and using the compound as a dopant in an organic light emitting layer (EML) of a multilayered OLED.

The invention claimed is:

1. An asymmetric styryl derivative represented by the following Formula 1:

[Formula 1]

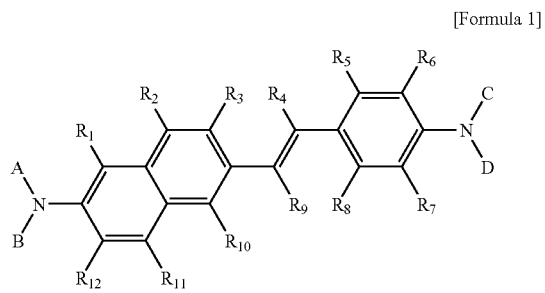

wherein, $R_1$ to $R_8$, and $R_{10}$ to $R_{12}$ may be the same or different, and each independently represents hydrogen, a substituted or unsubstituted $C_1$~$C_{30}$ alkyl group, a substituted or unsubstituted $C_1$~$C_{30}$ alkoxy group, a substituted or unsubstituted $C_6$~$C_{40}$ aryl group, a substituted or unsubstituted $C_6$~$C_{40}$ aryloxy group, a substituted or unsubstituted $C_1$~$C_{30}$ heterocyclic group, an amino group, an alkylamino group, a cyano group, a nitro group, a hydroxyl group, or a halogen atom;

$R_9$ represents hydrogen, a substituted or unsubstituted $C_1$~$C_{30}$ alkyl group, a substituted or unsubstituted $C_1$~$C_{30}$ alkoxy group, a substituted or unsubstituted $C_6$~$C_{40}$ aryloxy group, an amino group, an alkylamino group, a cyano group, a nitro group, a hydroxyl group, or a halogen atom;

A, B, C, and D may be the same or different, and each independently represents a substituted or unsubstituted phenyl group, a substituted or unsubstituted phenylene group, a substituted or unsubstituted naphthalene group, a substituted or unsubstituted $C_6$~$C_{40}$ aryl group, a substituted or unsubstituted biphenyl group, a substituted or unsubstituted anthracene group, or a substituted or unsubstituted $C_1$-$C_{30}$ alkyl group; and the substituted groups are each independently substituted with one or more substituents selected from the group consisting of a halogen atom, a $C_1$-$C_{30}$ alkyl group, a $C_1$-$C_{30}$ alkoxy group, a $C_6$-$C_{40}$ aryloxy group, a $C_6$-$C_{40}$ arylalkyl group, a nitro group, a cyano group, an amino group in which a hydrocarbon of $C_1$-$C_{30}$ is substituted, a $C_6$-$C_{40}$ aryl group, and a $C_1$-$C_{30}$ heterocyclic group.

2. An asymmetric styryl derivative selected from the group consisting of compounds represented by the following Formulas:

Ex-1
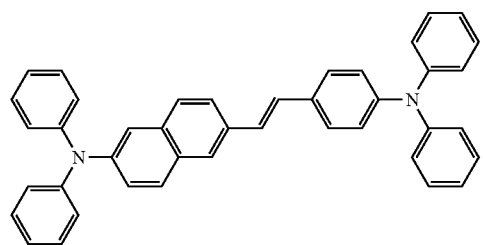
Ex-2
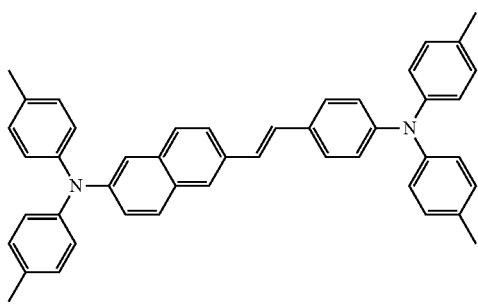
Ex-3
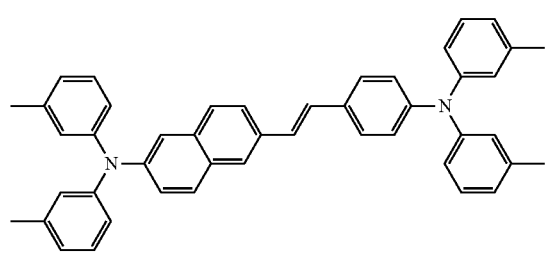
Ex-4
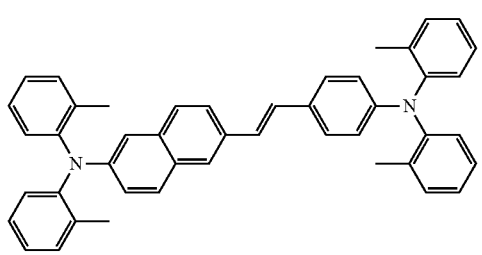
Ex-5
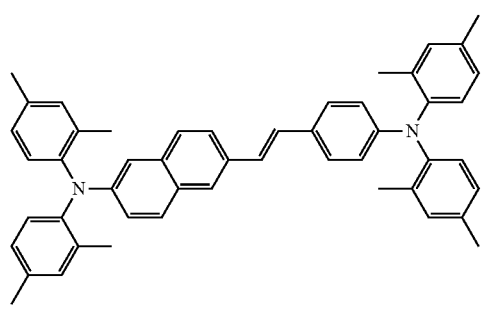
Ex-6
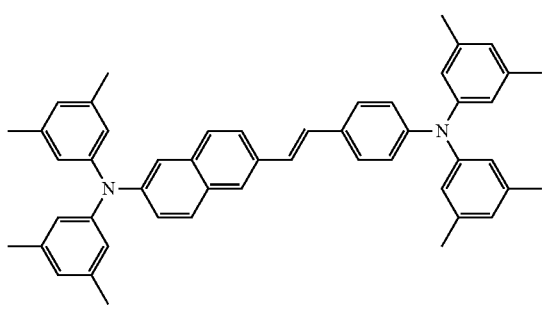
Ex-7
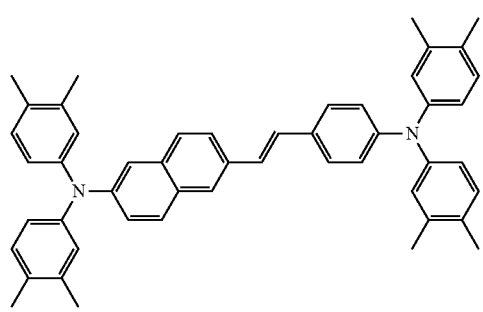
Ex-8
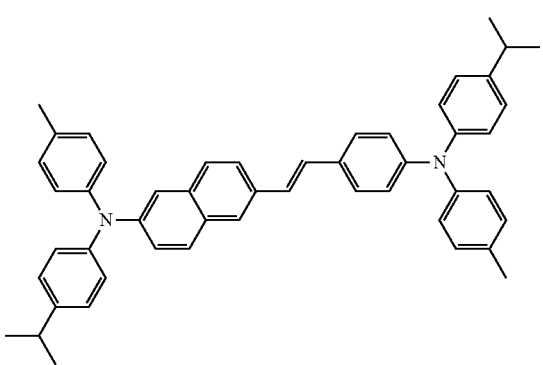

-continued
Ex-9
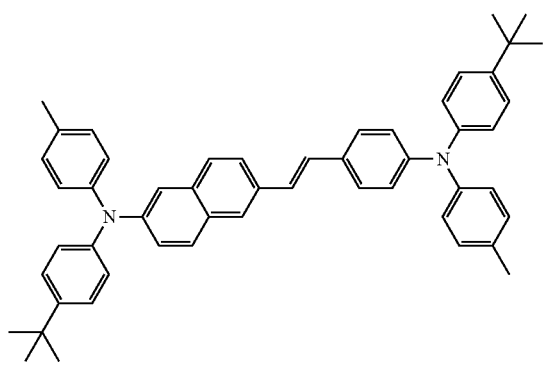
Ex-10
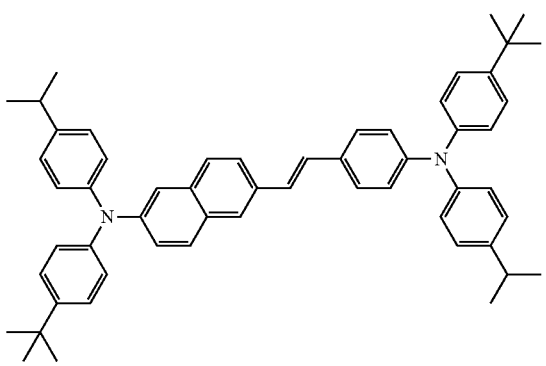
Ex-11
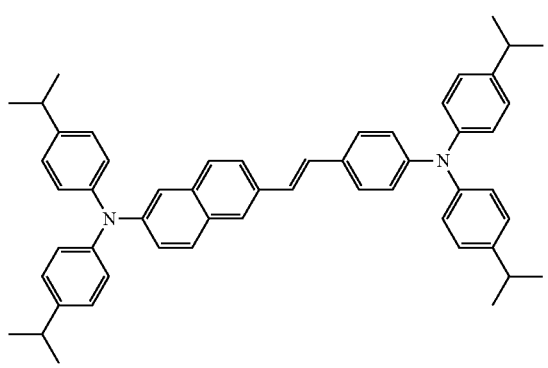
Ex-12
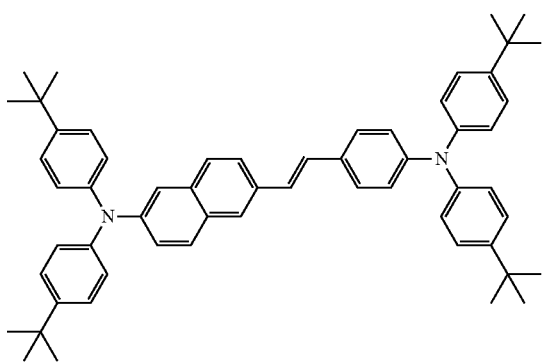
Ex-13
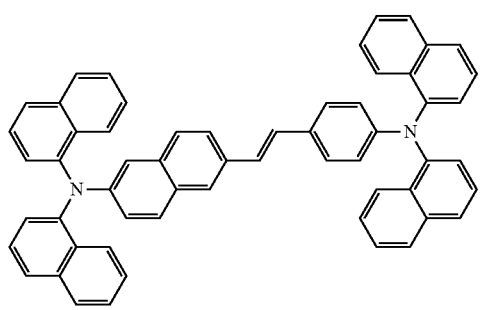
Ex-14
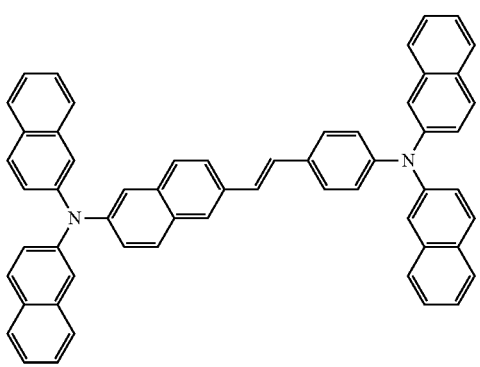
Ex-15
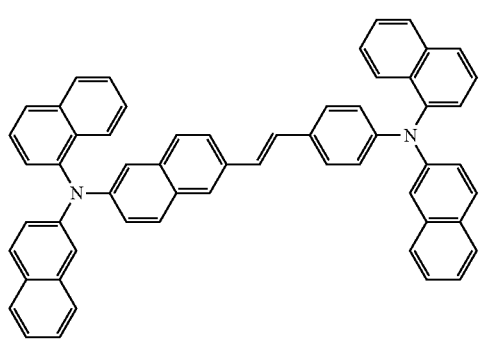
Ex-16
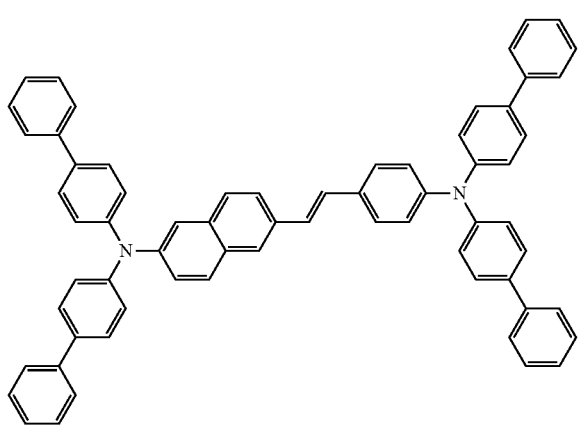

-continued
Ex-17
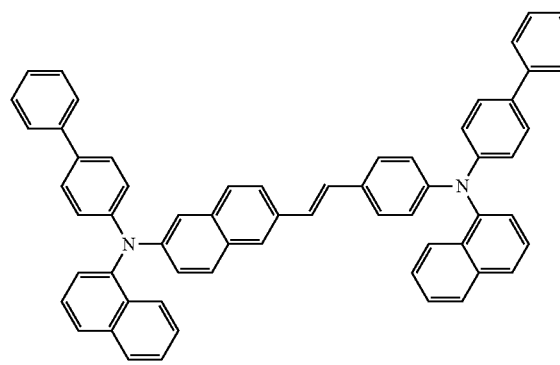
Ex-18
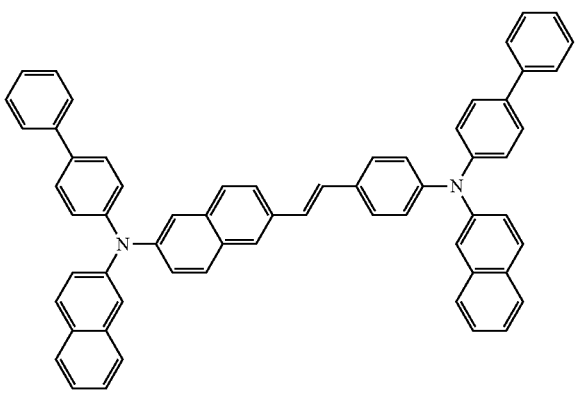
Ex-19
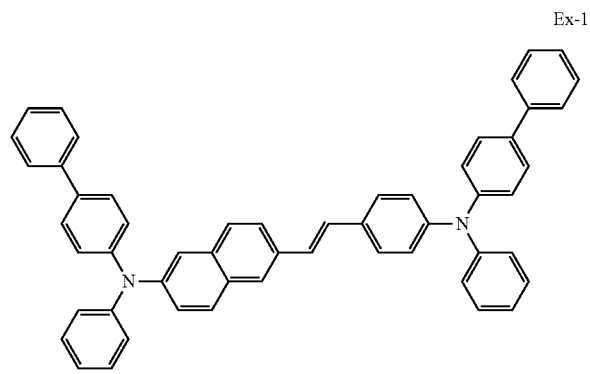
Ex-20
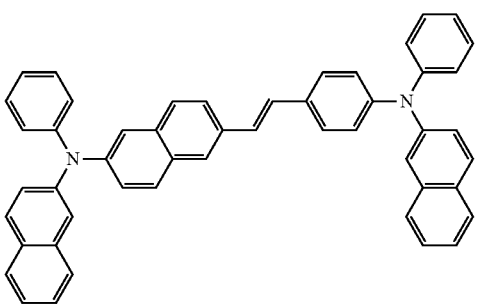
Ex-21
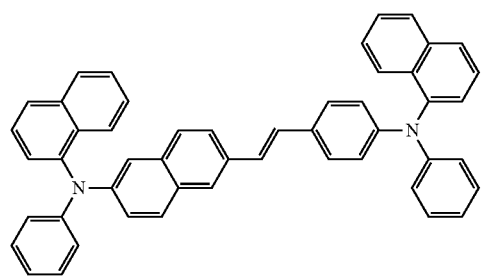
Ex-22
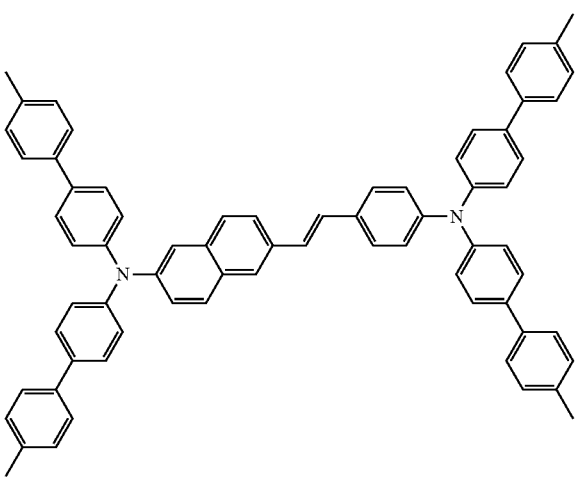

Ex-23
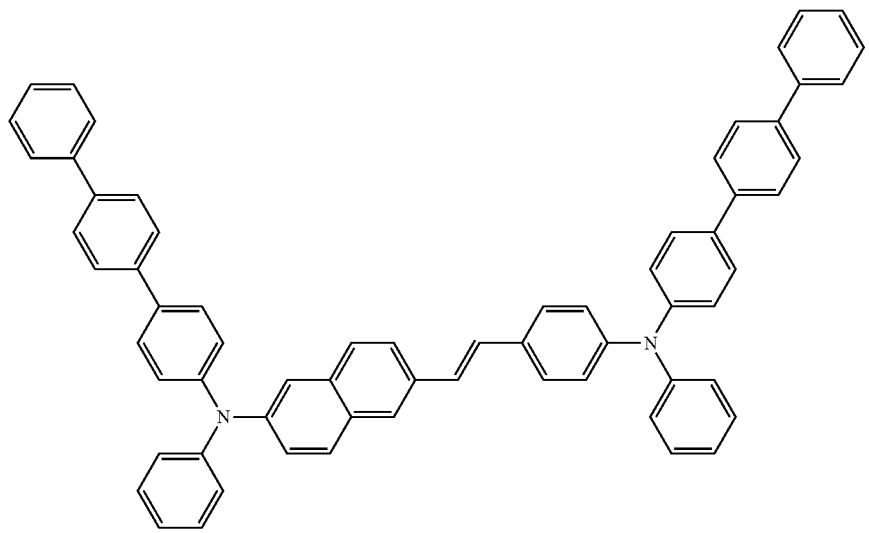
Ex-24
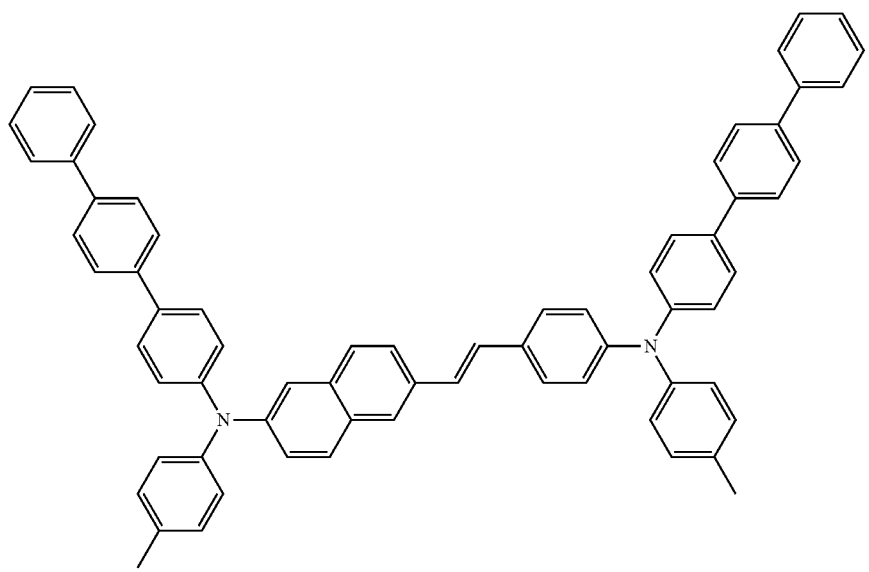
Ex-25
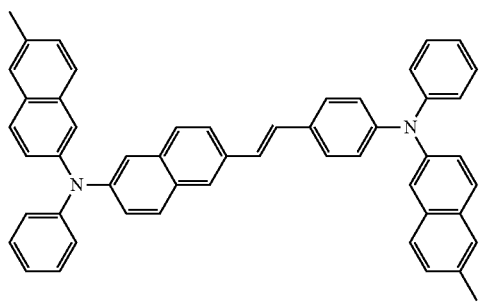
Ex-26
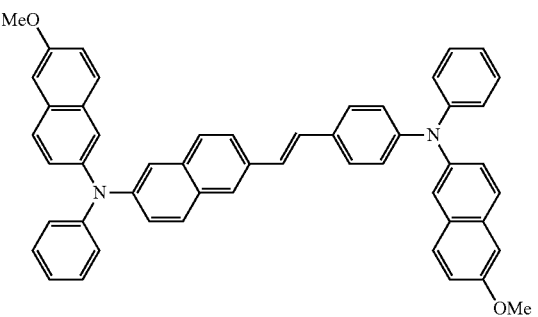

-continued
Ex-27
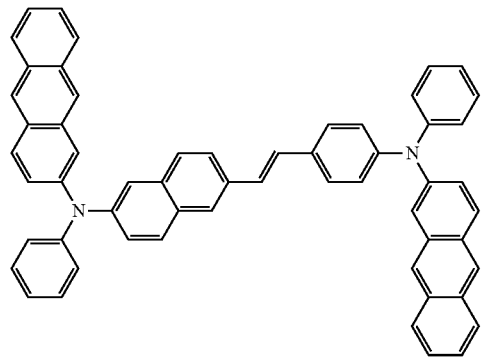
Ex-28
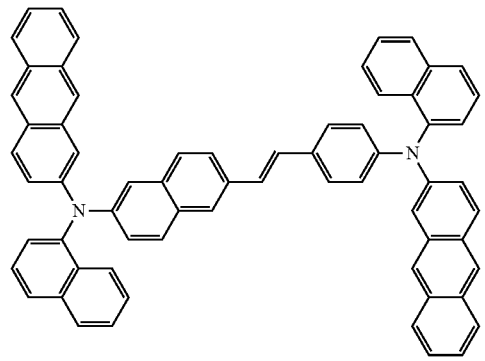
Ex-29
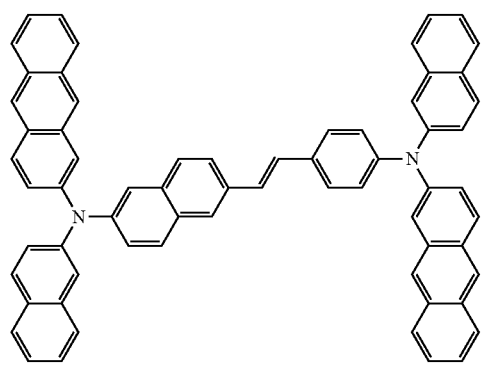
Ex-30
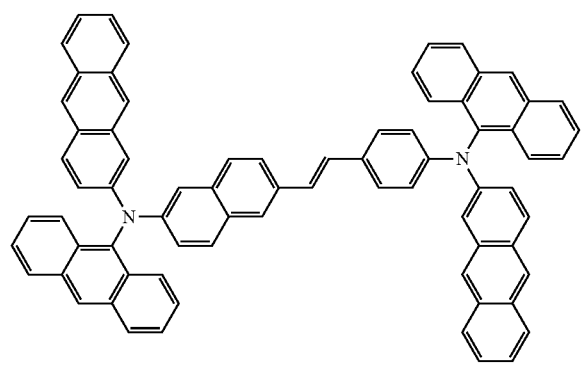
Ex-31
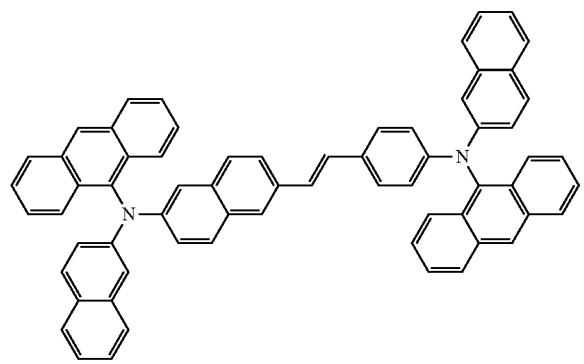
Ex-32
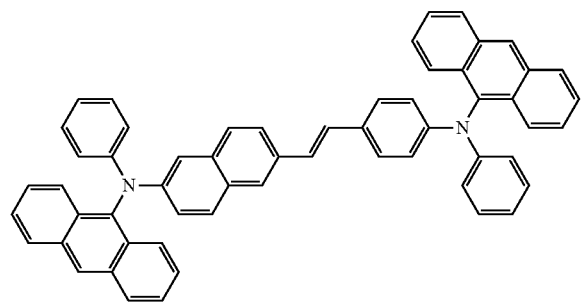
Ex-33
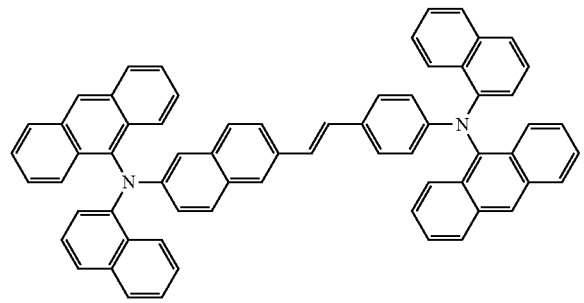
Ex-34
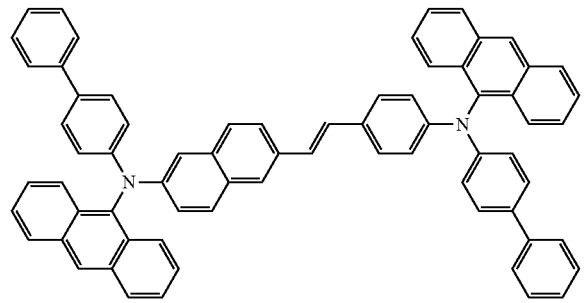

-continued
Ex-35
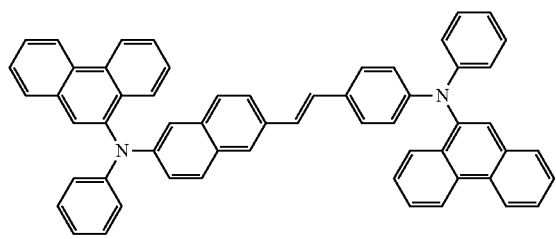
Ex-36
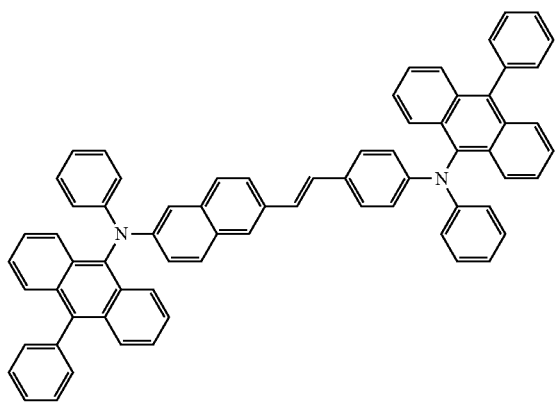
Ex-37
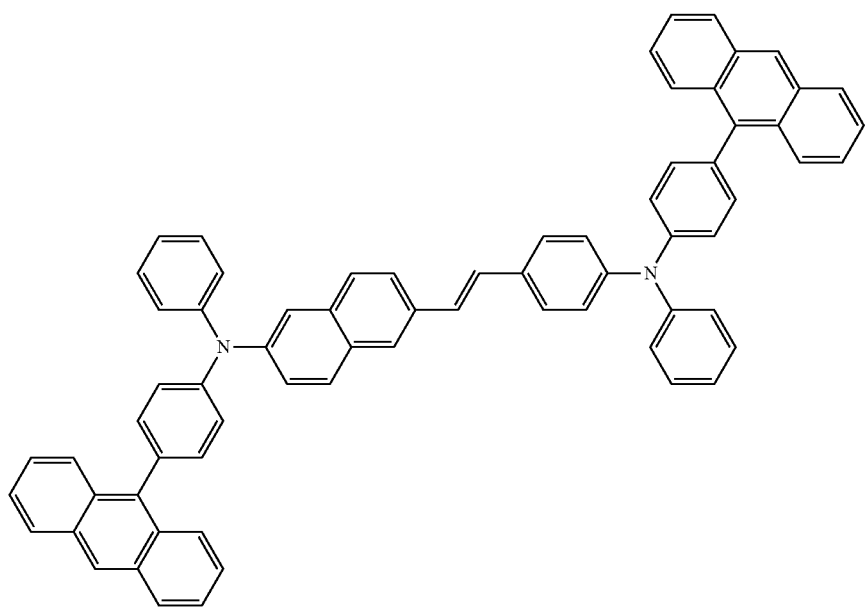
Ex-38
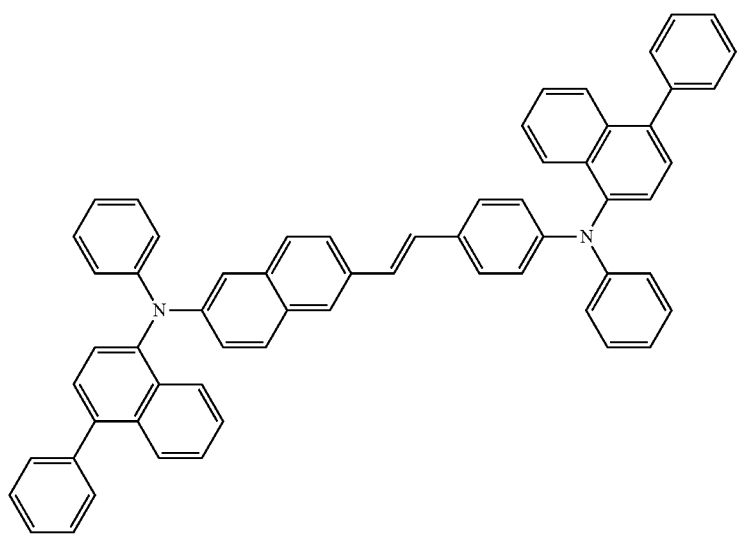

Ex-39

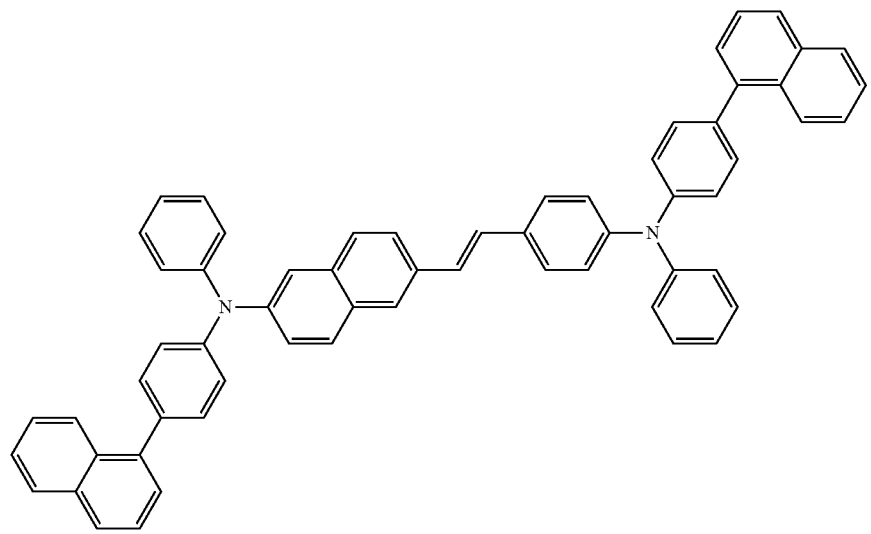

Ex-40

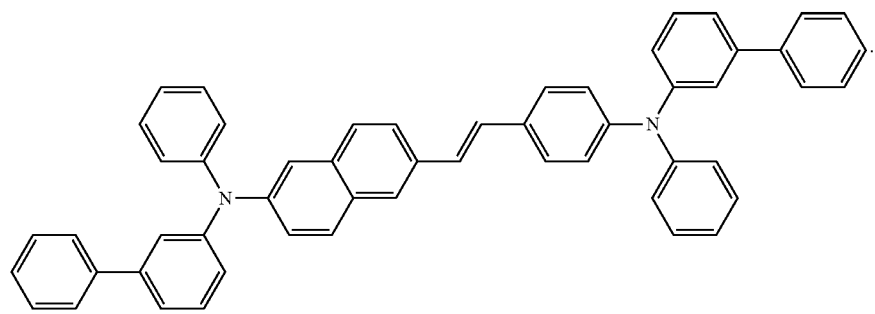

3. An organic light emitting layer comprising the asymmetric styryl derivative as claimed in claim 1, wherein the asymmetric styryl derivative is represented by the following Formula 1:

[Formula 1]

wherein, $R_1$ to $R_8$, and $R_{10}$ to $R_{12}$ may be the same or different, and each independently represents hydrogen, a substituted or unsubstituted $C_1$-$C_{30}$ alkyl group, a substituted or unsubstituted $C_1$-$C_{30}$ alkoxy group, a substituted or unsubstituted $C_6$-$C_{40}$ aryl group, a substituted or unsubstituted $C_6$-$C_{40}$ aryloxy group, a substituted or unsubstituted $C_1$-$C_{30}$ heterocyclic group, an amino group, an alkylamino group, a cyano group, a nitro group, a hydroxyl group, or a halogen atom;

$R_9$ represents hydrogen, a substituted or unsubstituted $C_1$~$C_{30}$ alkyl group, a substituted or unsubstituted $C_1$~$C_{30}$ alkoxy group, a substituted or unsubstituted $C_6$~$C_{40}$ aryloxy group, an amino group, an alkylamino group, a cyano group, a nitro group, a hydroxyl group, or a halogen atom;

A, B, C, and D may be the same or different, and each independently represents a substituted or unsubstituted phenyl group, a substituted or unsubstituted phenylene group, a substituted or unsubstituted naphthalene group, a substituted or unsubstituted $C_6$-$C_{40}$ aryl group, a substituted or unsubstituted biphenyl group, a substituted or unsubstituted anthracene group, or a substituted or unsubstituted $C_1$-$C_{30}$ alkyl group; and the substituted groups are each independently substituted with one or more substituents selected from the group consisting of a halogen atom, a $C_1$-$C_{30}$ alkyl group, a $C_1$-$C_{30}$ alkoxy group, a $C_6$-$C_{40}$ aryloxy group, a $C_6$-$C_{40}$ arylalkyl group, a nitro group, a cyano group, an amino group in which a hydrocarbon of $C_1$~$C_{30}$ is substituted, a $C_6$-$C_{40}$ aryl group, and a $C_1$-$C_{30}$ heterocyclic group.

4. An organic light emitting diode comprising the organic light emitting layer, wherein the organic light emitting layer comprises a asymmetric styryl derivative represented by the following Formula 1:

[Formula 1]

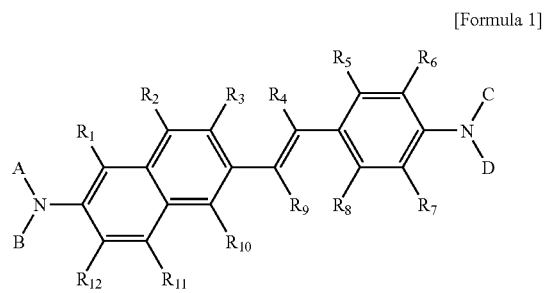

wherein, $R_1$ to $R_8$, and $R_{10}$ to $R_{12}$ may be the same or different, and each independently represents hydrogen, a substituted or unsubstituted $C_1$-$C_{30}$ alkyl group, a substituted or unsubstituted $C_1$-$C_{30}$ alkoxy group, a substituted or unsubstituted $C_6$-$C_{40}$ aryl group, a substituted or unsubstituted $C_6$-$C_{40}$ aryloxy group, a substituted or unsubstituted $C_1$-$C_{30}$ heterocyclic group, an amino group, an alkylamino group, a cyano group, a nitro group, a hydroxyl group, or a halogen atom;

$R_9$ represents hydrogen, a substituted or unsubstituted $C_1$-$C_{30}$ alkyl group, a substituted or unsubstituted $C_1$-$C_{30}$ alkoxy group, a substituted or unsubstituted $C_6$-$C_{40}$ aryloxy group, an amino group, an alkylamino group, a cyano group, a nitro group, a hydroxyl group, or a halogen atom;

A, B, C, and D may be the same or different, and each independently represents a substituted or unsubstituted phenyl group, a substituted or unsubstituted phenylene group, a substituted or unsubstituted naphthalene group, a substituted or unsubstituted $C_6$-$C_{40}$ aryl group, a substituted or unsubstituted biphenyl group, a substituted or unsubstituted anthracene group, or a substituted or unsubstituted $C_1$-$C_{30}$ alkyl group; and the substituted groups are each independently substituted with one or more substituents selected from the group consisting of a halogen atom, a $C_1$-$C_{30}$ alkyl group, a $C_1$-$C_{30}$ alkoxy group, a $C_6$-$C_{40}$ aryloxy group, a $C_6$-$C_{40}$ arylalkyl group, a nitro group, a cyano group, an amino group in which a hydrocarbon of $C_1$-$C_{30}$ is substituted, a $C_6$-$C_{40}$ aryl group, and a $C_1$-$C_{30}$ heterocyclic group.

5. An organic light emitting layer as claimed in claim 2, wherein the asymmetric styryl derivative is selected from the group consisting of compounds represented by the following Formulas:

Ex-1

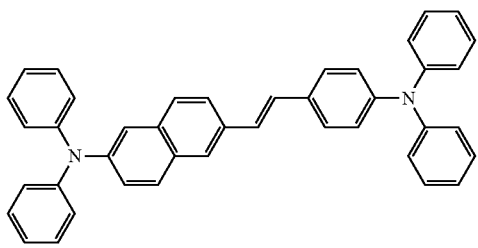

Ex-2

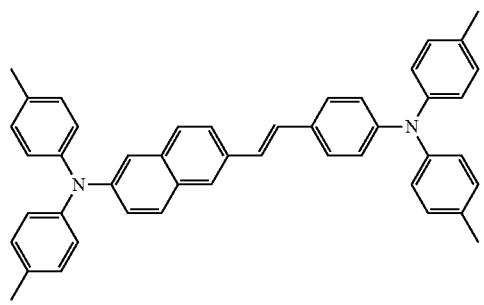

Ex-3

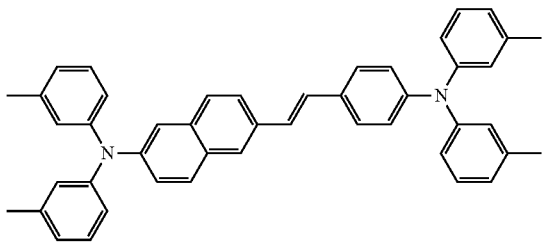

Ex-4

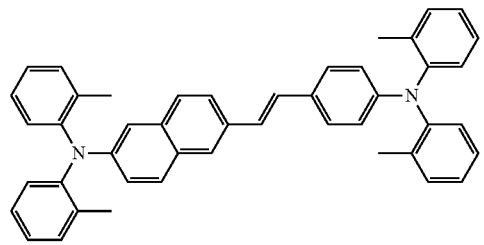

Ex-5

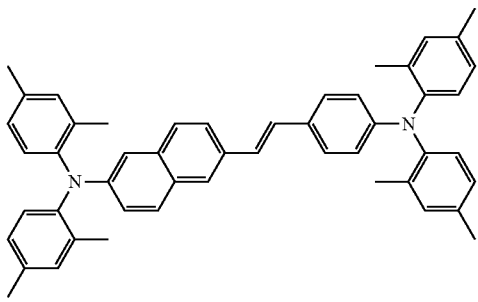

Ex-6

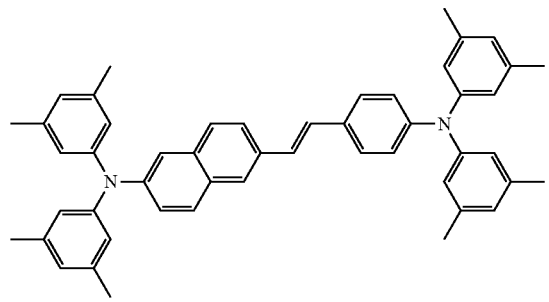

-continued
Ex-7
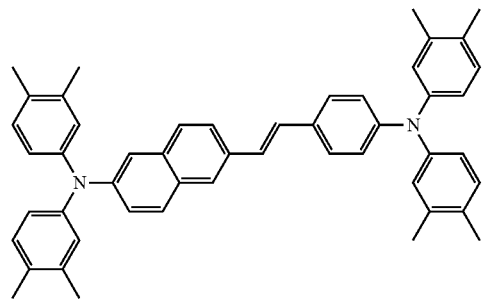
Ex-8
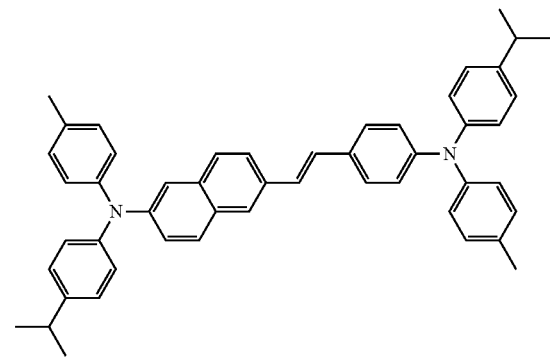
Ex-9
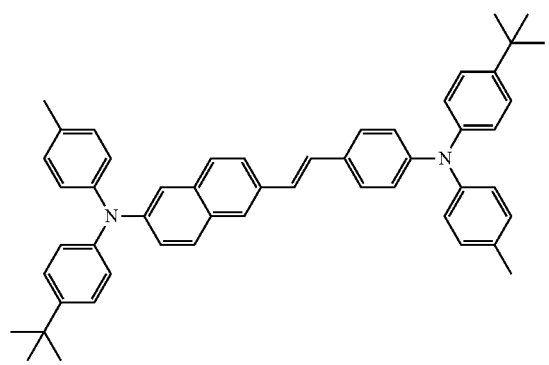
Ex-10
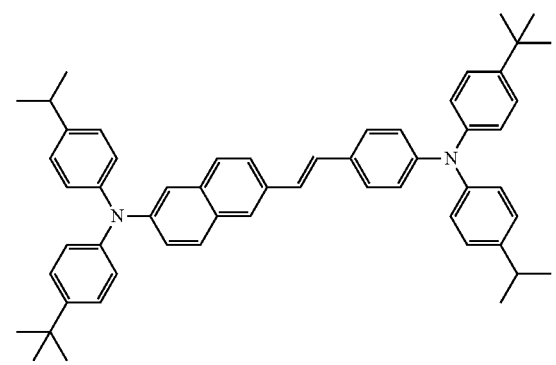
Ex-11
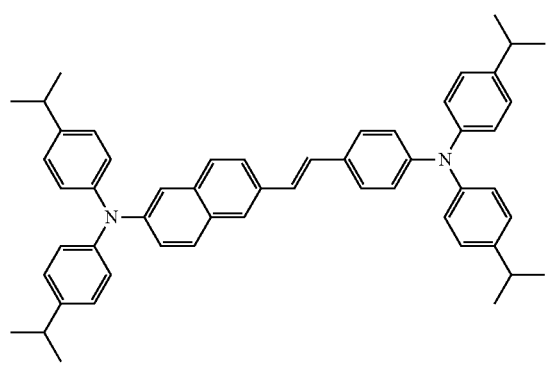
Ex-12
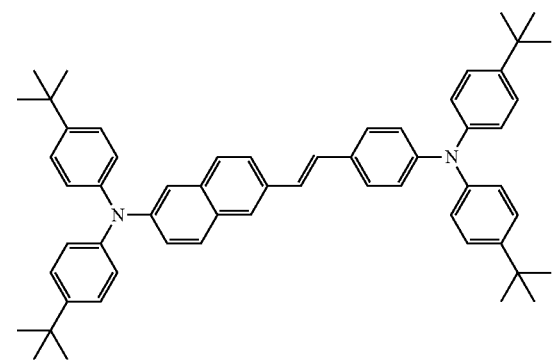
Ex-13
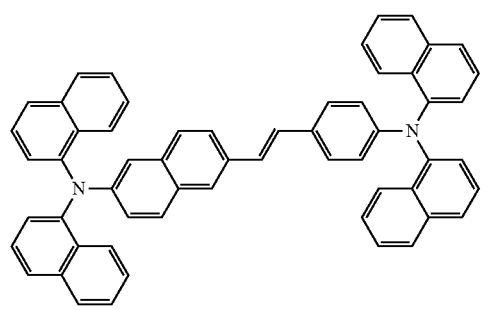
Ex-14
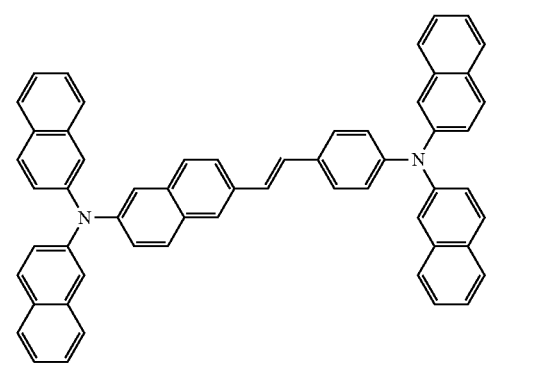

-continued
Ex-15
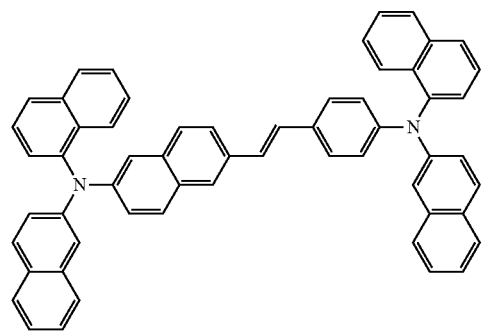
Ex-16
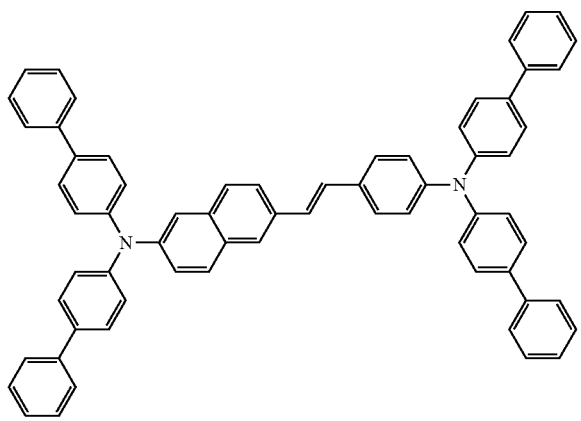
Ex-17
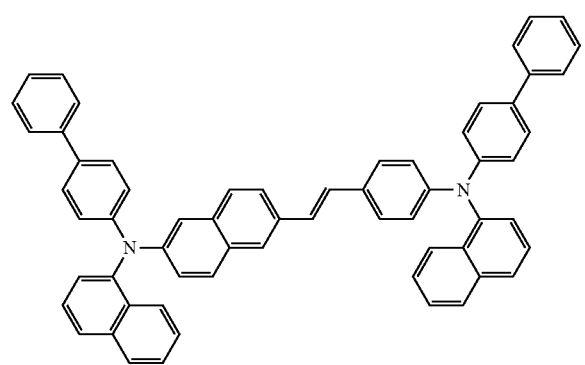
Ex-18
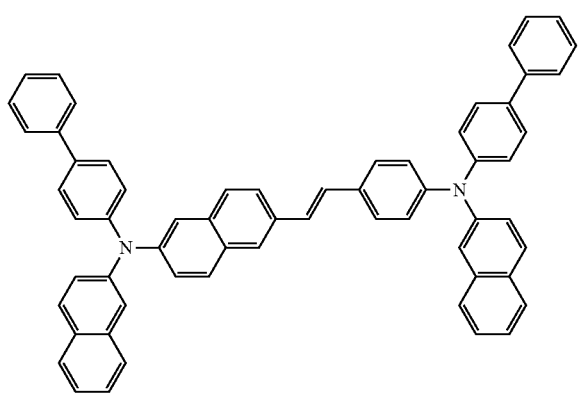
Ex-19
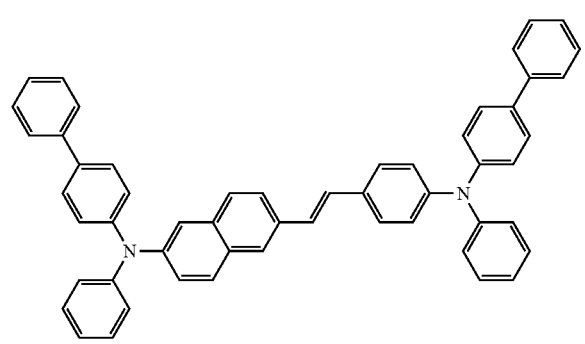
Ex-20
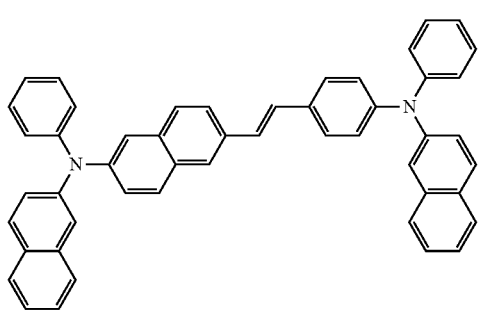

-continued
Ex-21
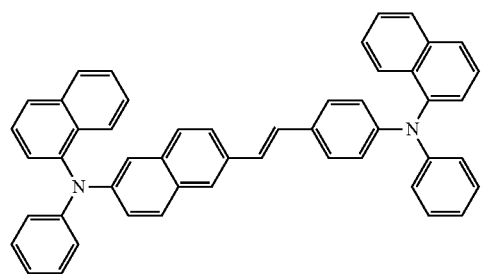
Ex-22
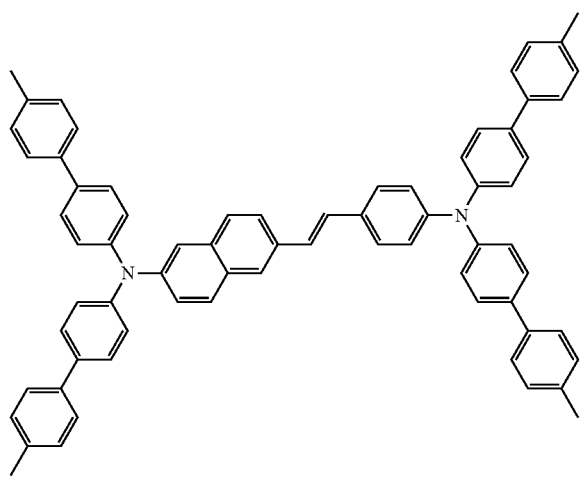
Ex-23
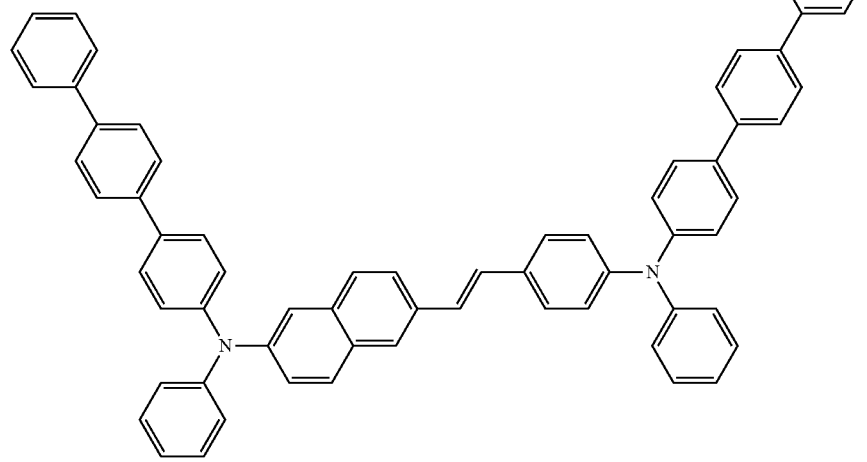
Ex-24
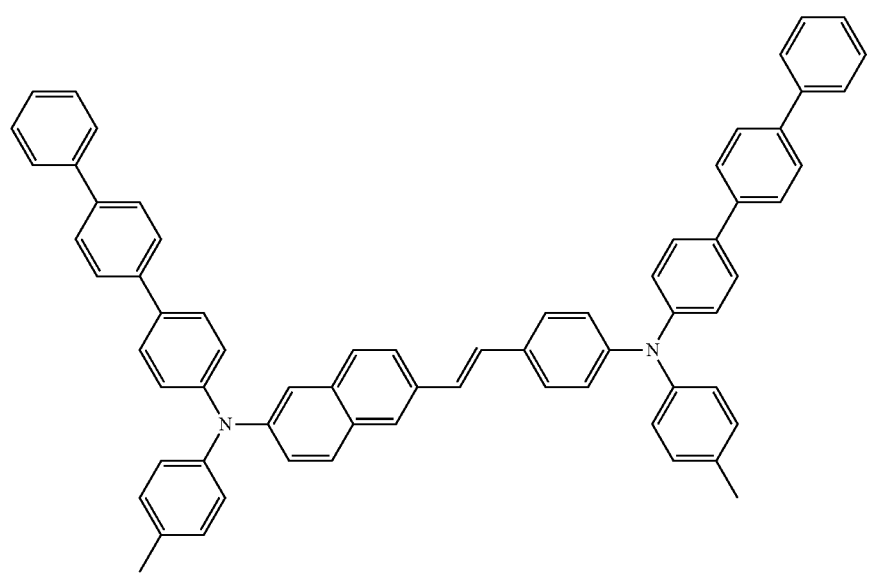

-continued
Ex-25
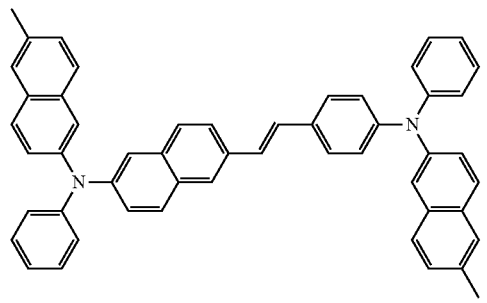
Ex-26
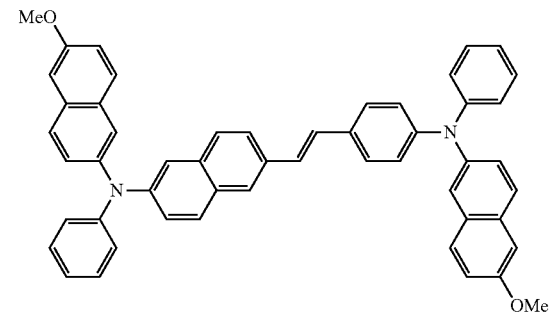
Ex-27
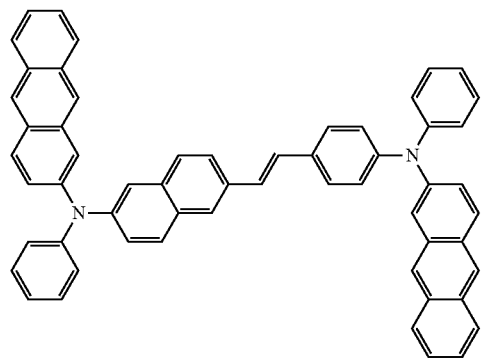
Ex-28
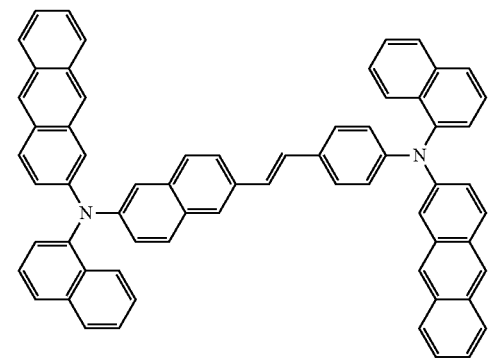
Ex-29
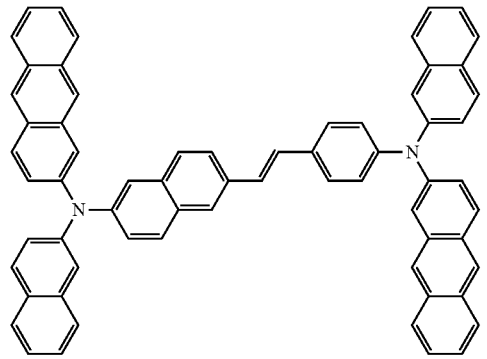
Ex-30
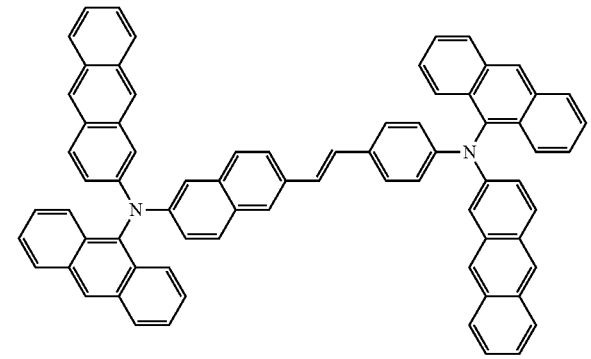
Ex-31
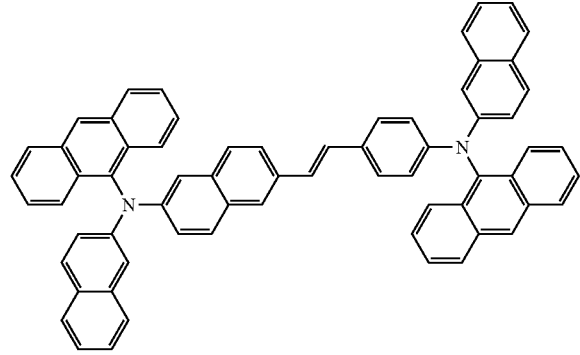
Ex-32
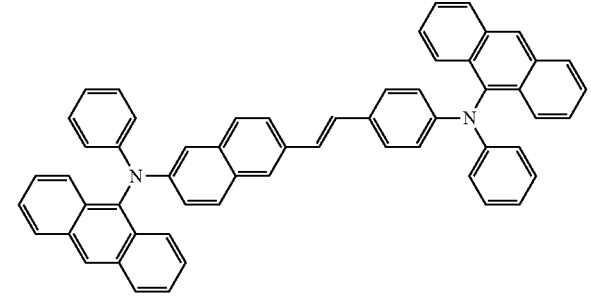

-continued
Ex-33
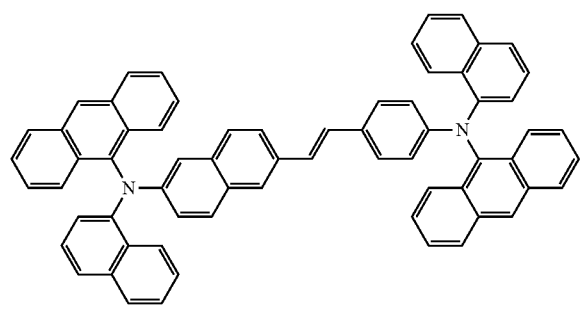
Ex-34
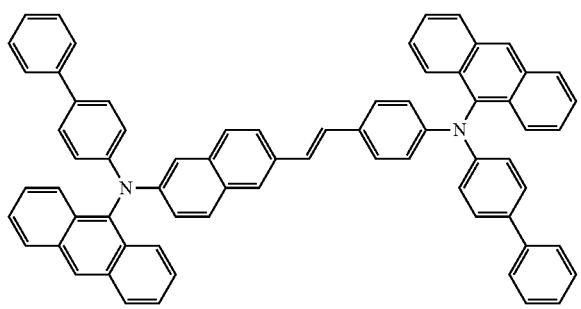
Ex-35
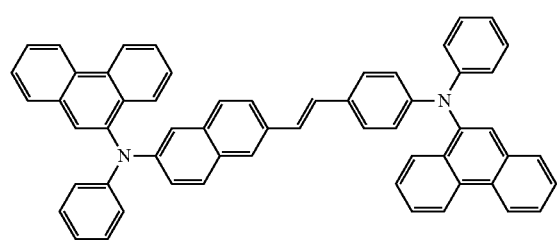
Ex-36
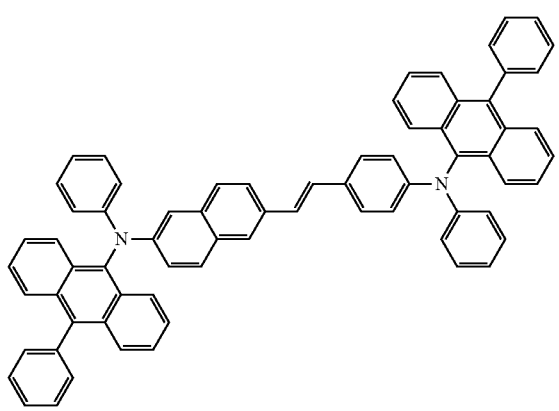
Ex-37
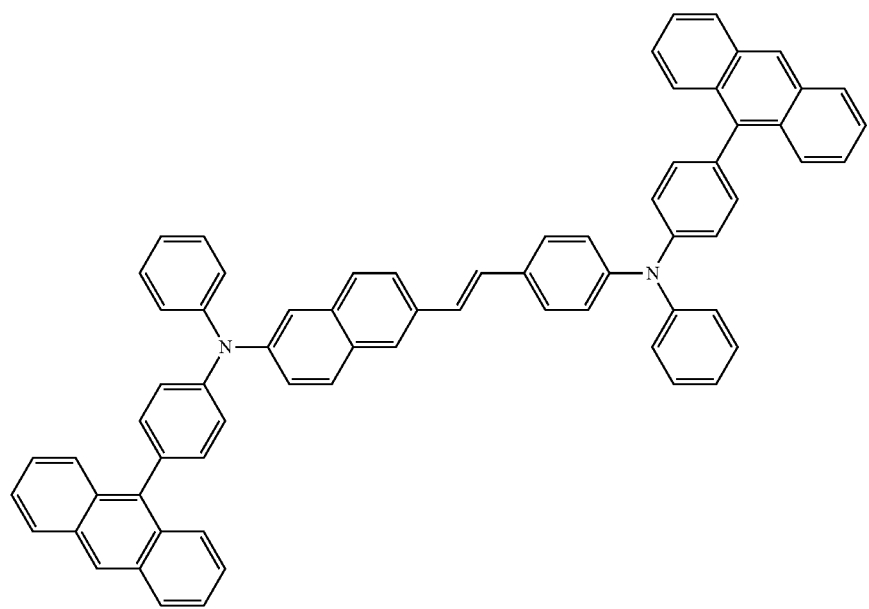

-continued
Ex-38
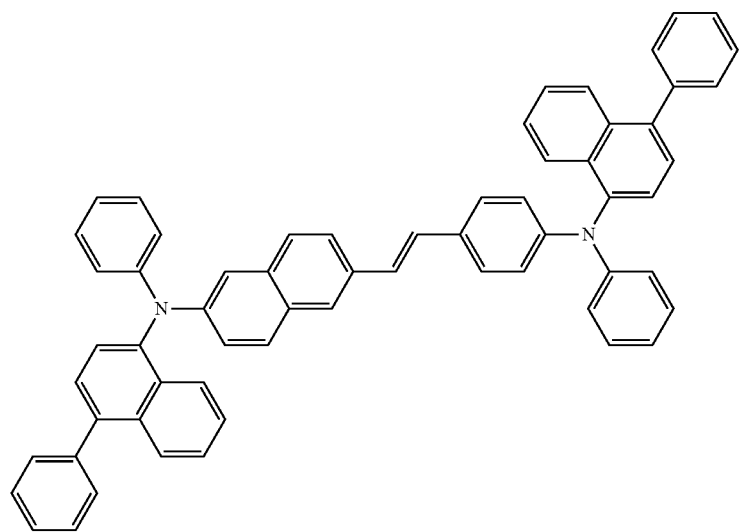
Ex-39
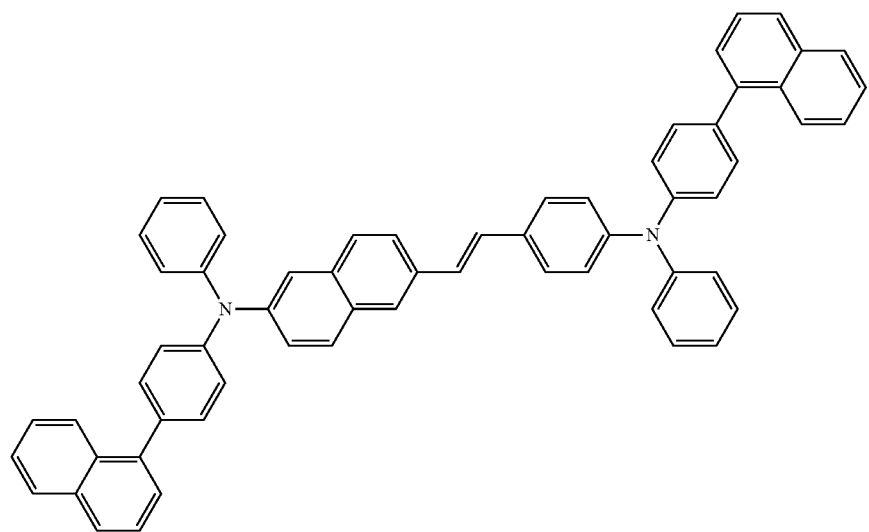
Ex-40
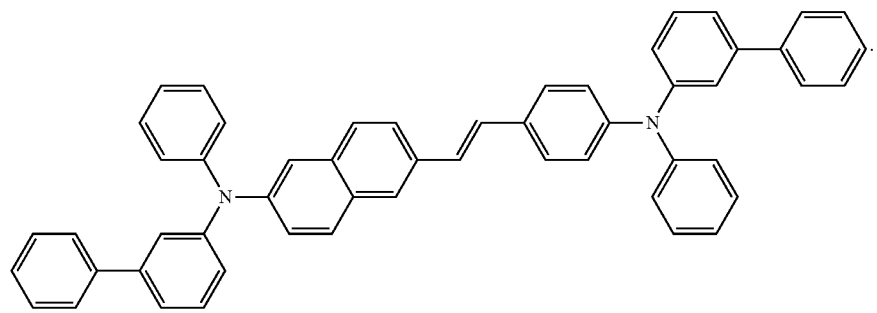

6. An organic light emitting diode comprising the organic light emitting layer, which comprises the asymmetric styryl derivative as claimed in claim 2, wherein the asymmetric styryl derivative is selected from the group consisting of compounds represented by the following Formulas:
Ex-1
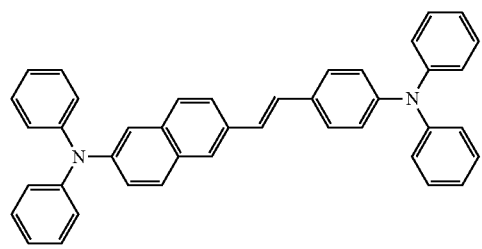
Ex-2
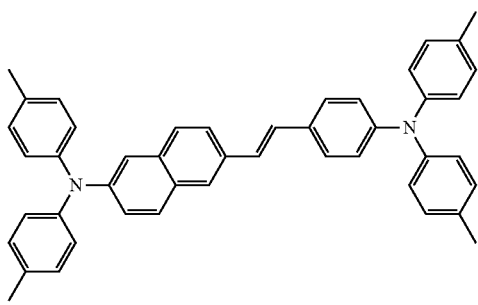
Ex-3
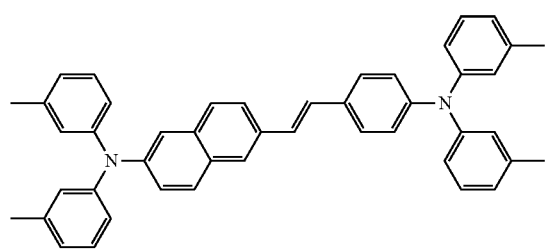
Ex-4
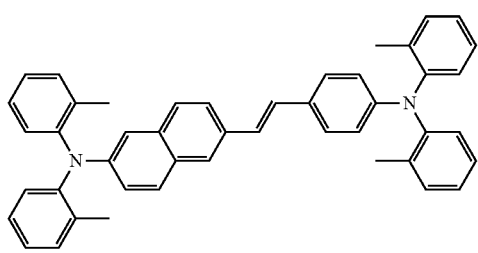
Ex-5
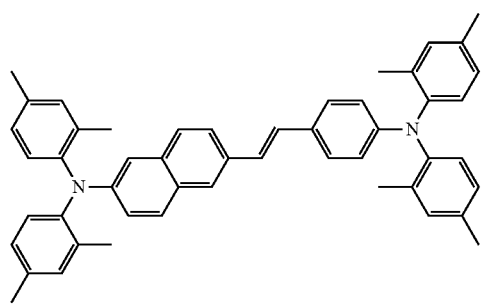
Ex-6
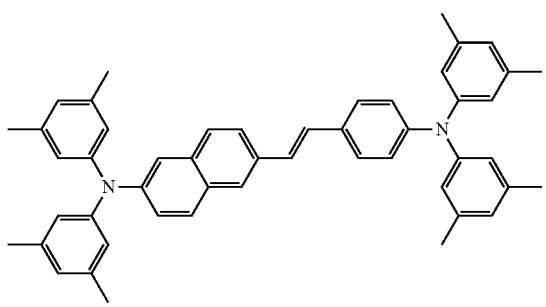
Ex-7
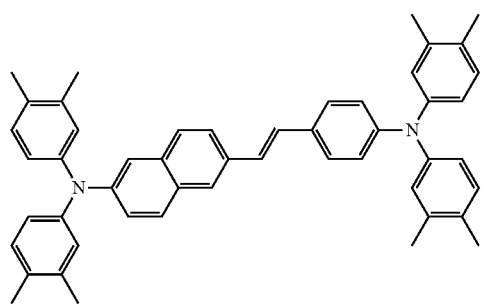
Ex-8
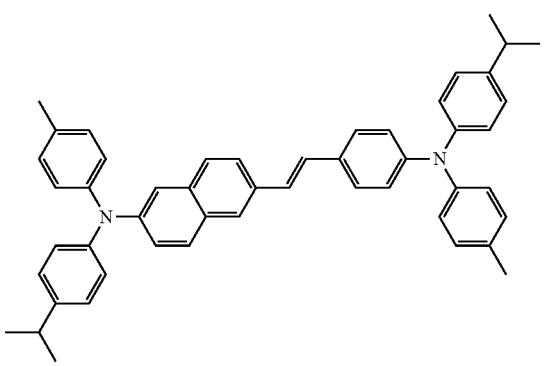

-continued
Ex-9
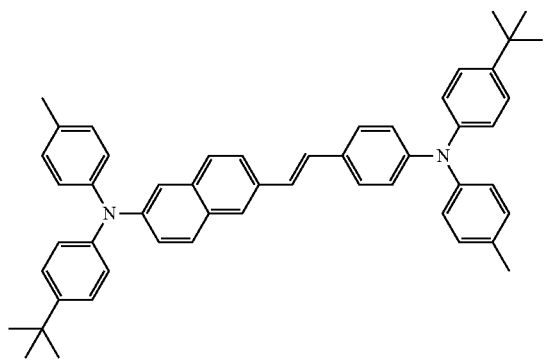
Ex-10
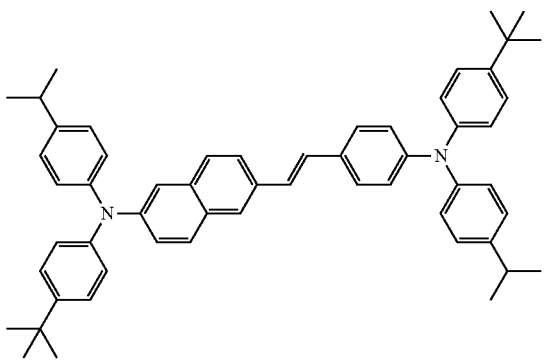
Ex-11
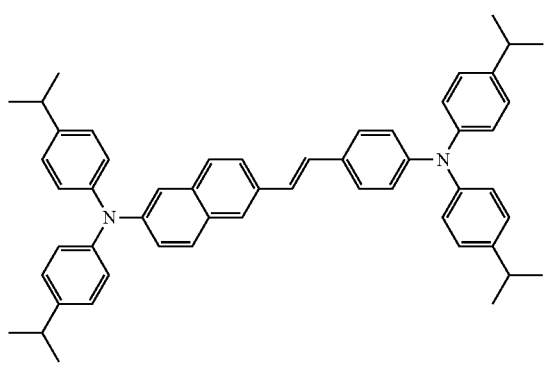
Ex-12
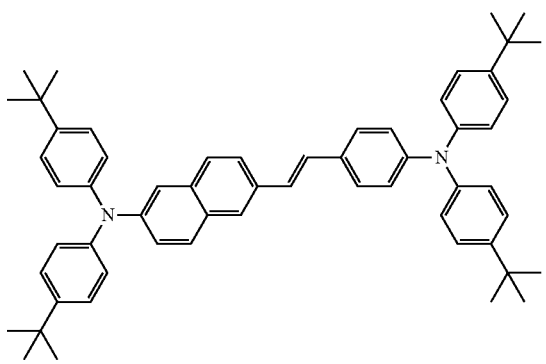
Ex-13
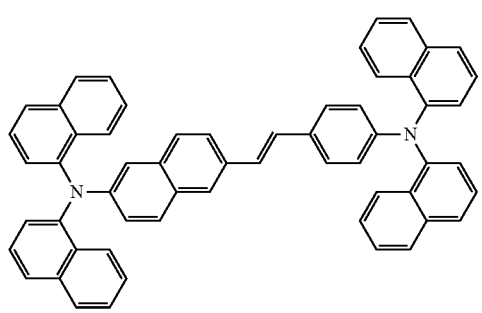
Ex-14
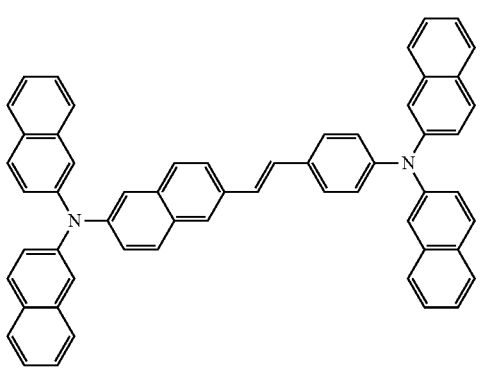
Ex-15
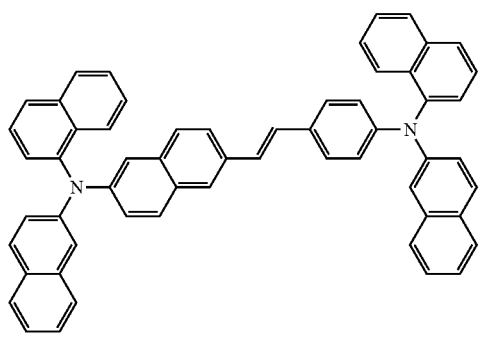
Ex-16
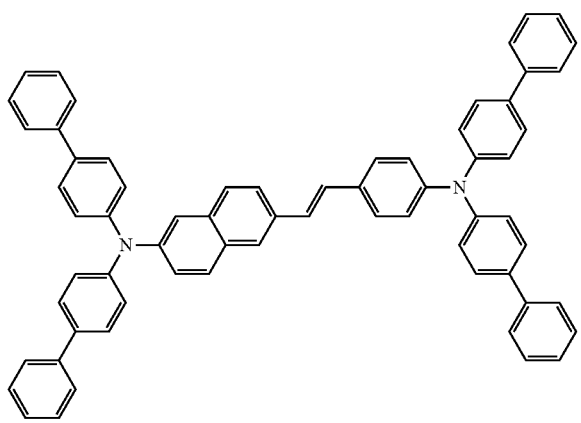

-continued
Ex-17
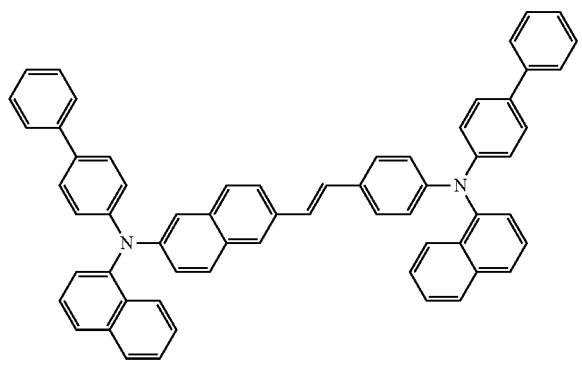
Ex-18
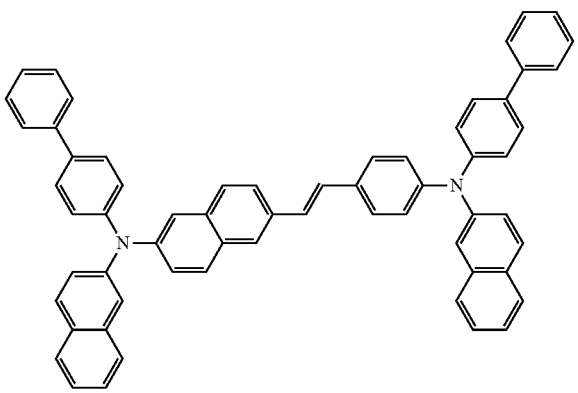
Ex-19
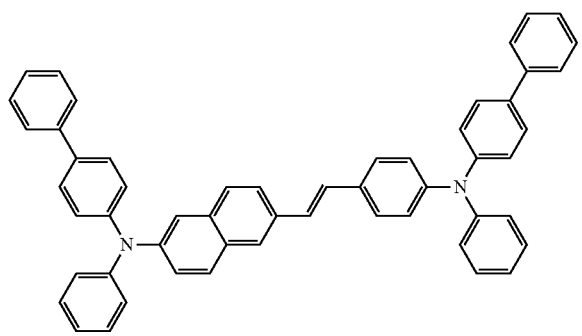
Ex-20
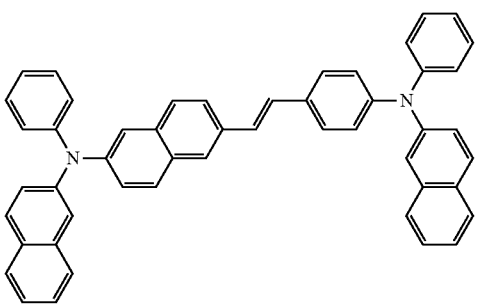
Ex-21
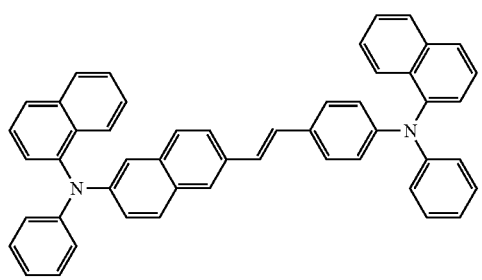
Ex-22
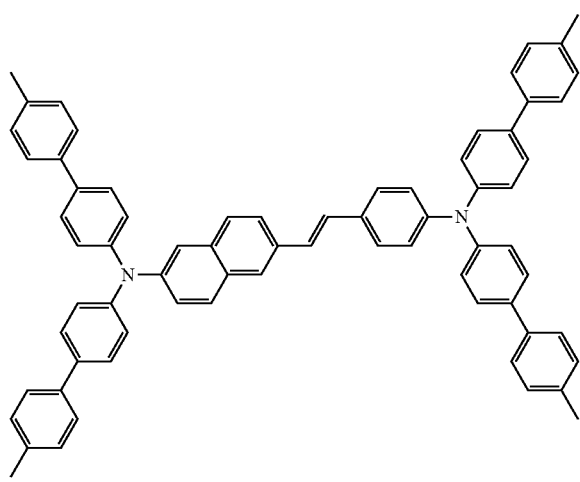

Ex-23
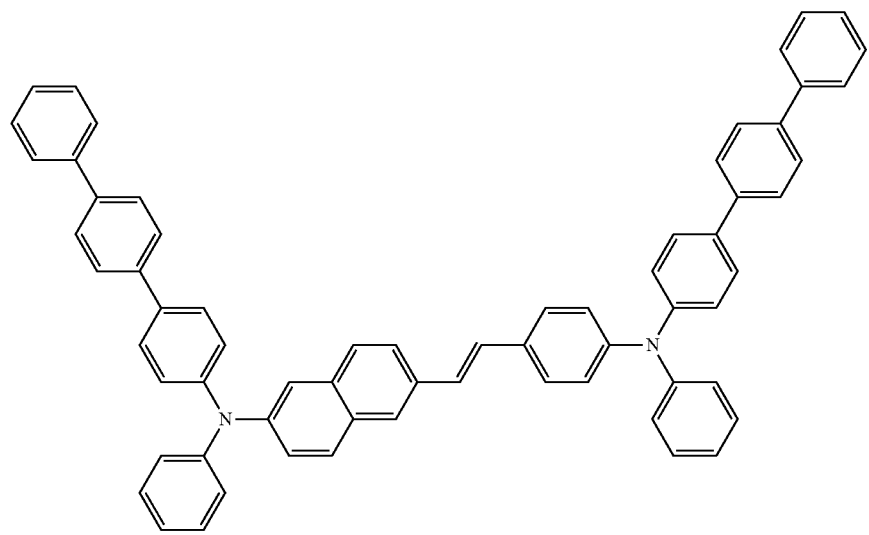
Ex-24
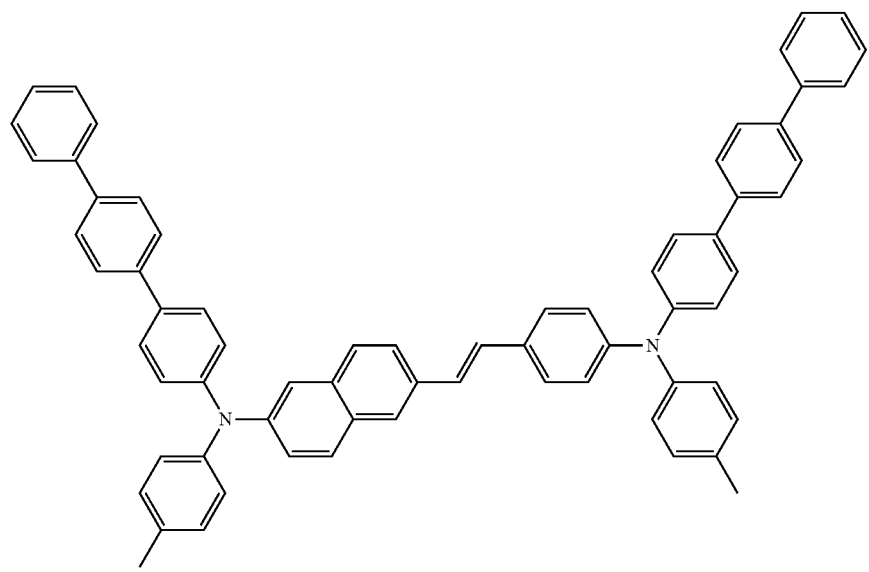
Ex-25
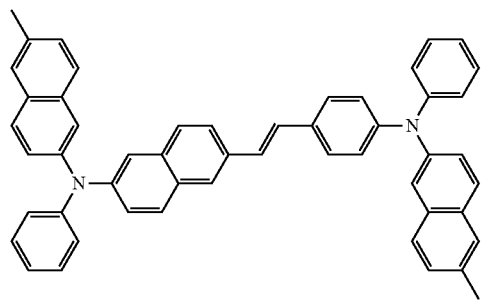
Ex-26
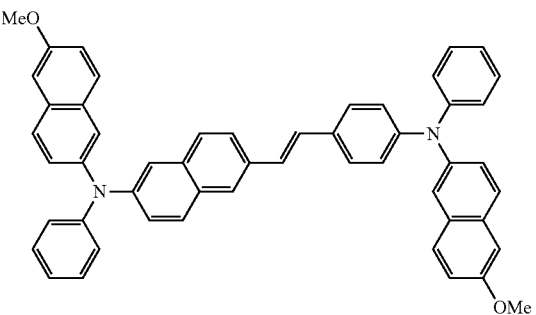

-continued
Ex-27
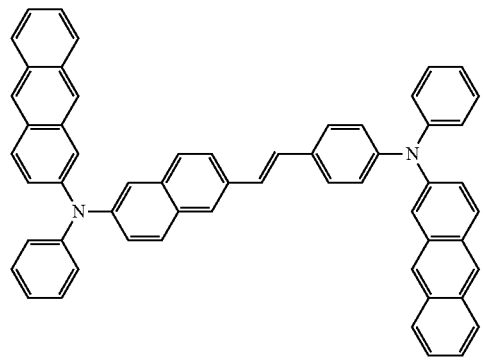
Ex-28
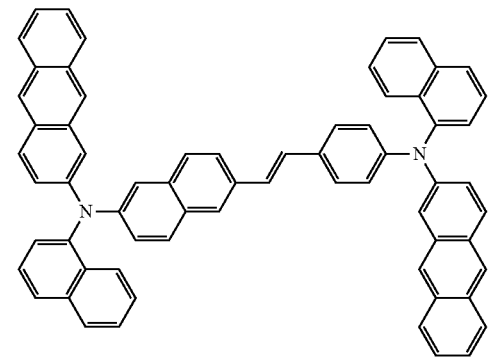
Ex-29
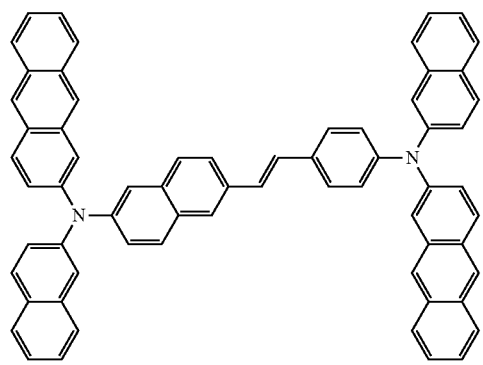
Ex-30
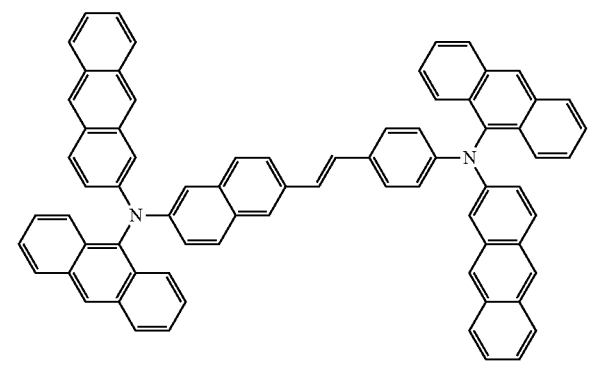
Ex-31
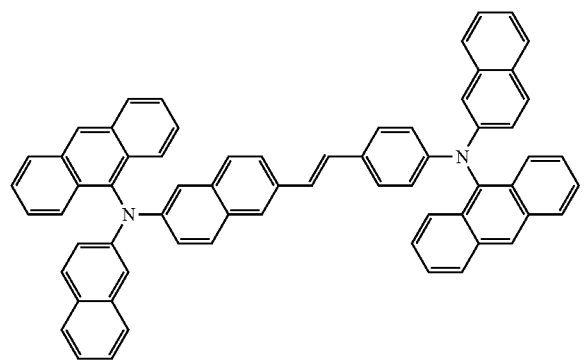
Ex-32
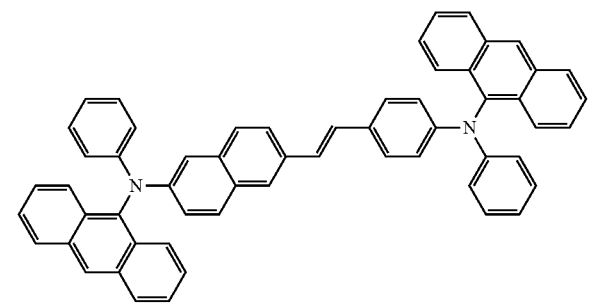
Ex-33
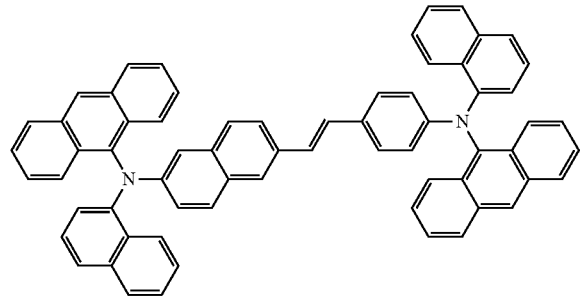
Ex-34
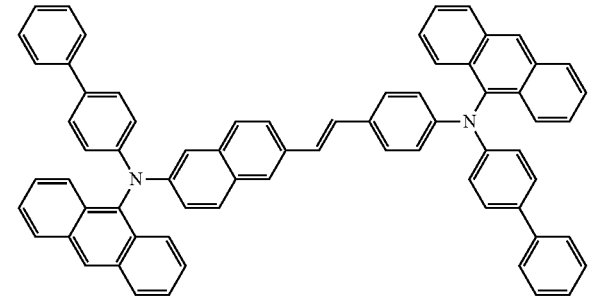

-continued
Ex-35
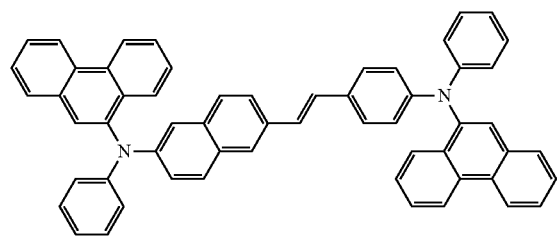
Ex-36
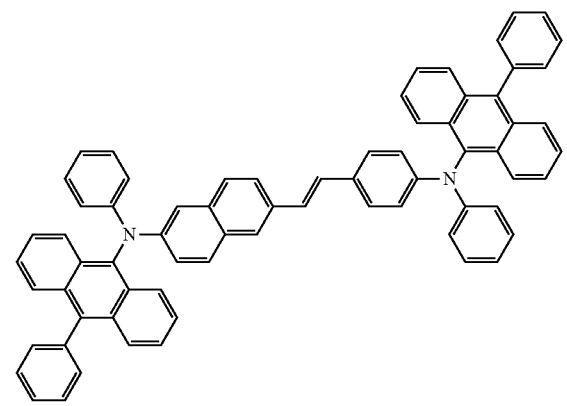
Ex-37
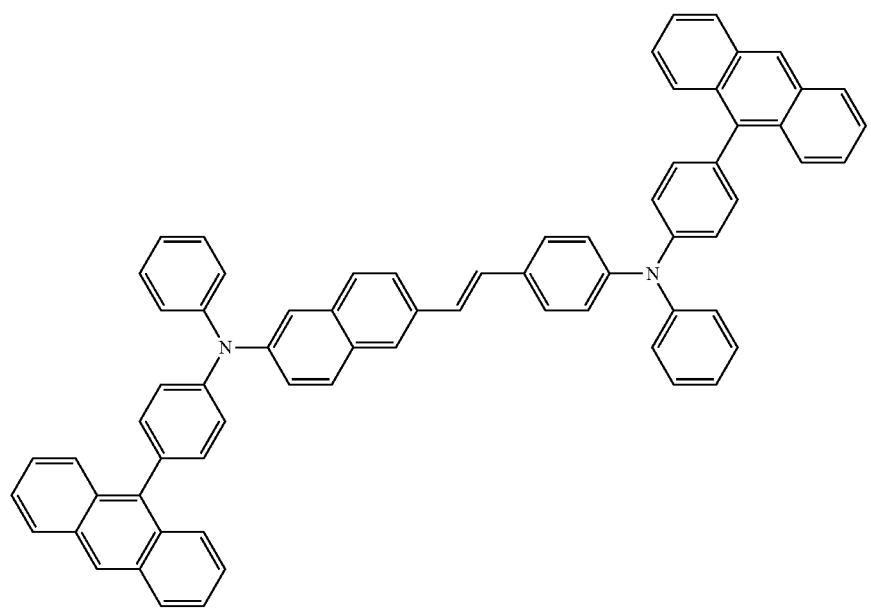
Ex-38
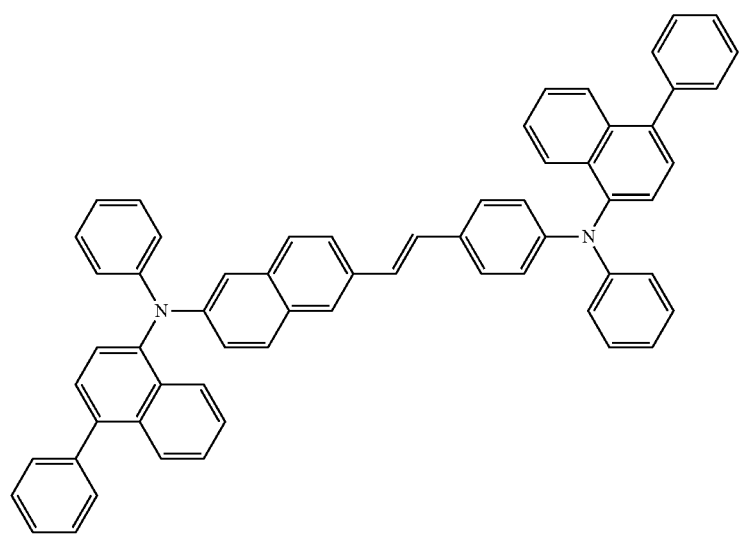

-continued
Ex-39
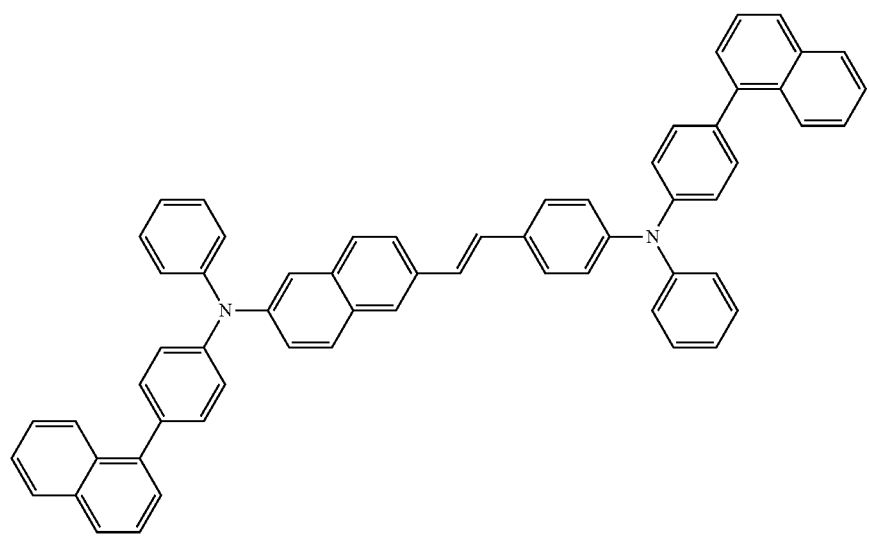
Ex-40
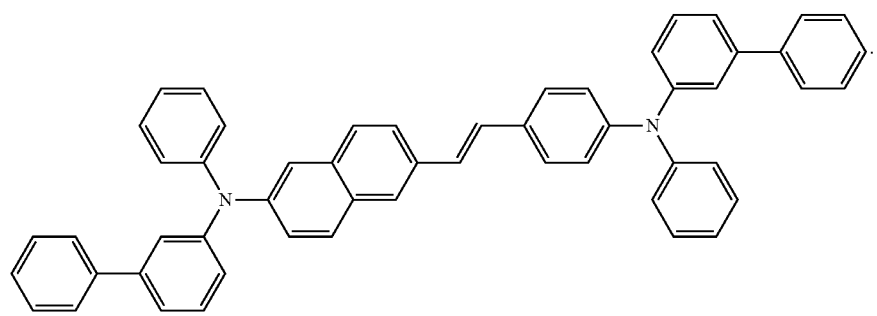
* * * * *